United States Patent
Dahlquist et al.

(10) Patent No.: US 8,658,851 B2
(45) Date of Patent: Feb. 25, 2014

(54) DEVICES WITH CELLS CULTURED ON FLEXIBLE SUPPORTS

(75) Inventors: John Dahlquist, Sudbury, MA (US); Susan Schaeffer, Wayland, MA (US)

(73) Assignee: Keracure, Inc., Chicago, IL (US)

( * ) Notice: Subject to any disclaimer, the term of this patent is extended or adjusted under 35 U.S.C. 154(b) by 694 days.

(21) Appl. No.: 12/445,962

(22) PCT Filed: Oct. 22, 2007

(86) PCT No.: PCT/US2007/082119
§ 371 (c)(1), (2), (4) Date: May 11, 2009

(87) PCT Pub. No.: WO2008/060822
PCT Pub. Date: May 22, 2008

(65) Prior Publication Data
US 2010/0196444 A1    Aug. 5, 2010

Related U.S. Application Data

(60) Provisional application No. 60/862,355, filed on Oct. 20, 2006, provisional application No. 60/943,916, filed on Jun. 14, 2007.

(51) Int. Cl.
- A61F 13/00  (2006.01)
- C12N 5/071  (2010.01)
- C12N 5/077  (2010.01)
- C12N 5/02   (2006.01)

(52) U.S. Cl.
USPC .............. 602/41; 602/47; 602/48; 602/58; 435/366; 435/371; 435/401; 435/402

(58) Field of Classification Search
None
See application file for complete search history.

(56) References Cited

U.S. PATENT DOCUMENTS

| | | | | |
|---|---|---|---|---|
| 3,867,939 A | * | 2/1975 | Moore et al. | 604/291 |
| 3,888,248 A | * | 6/1975 | Moore et al. | 602/43 |
| 5,122,470 A | | 6/1992 | Banes | |
| 5,250,042 A | * | 10/1993 | Torgalkar et al. | 604/333 |
| 6,039,972 A | * | 3/2000 | Barlow et al. | 424/445 |
| 6,440,452 B2 | * | 8/2002 | Rees et al. | 424/443 |
| 6,576,019 B1 | * | 6/2003 | Atala | 623/23.65 |
| 7,056,503 B2 | * | 6/2006 | Rees et al. | 424/93.21 |
| 7,569,076 B2 | * | 8/2009 | Atala | 623/23.65 |

(Continued)

FOREIGN PATENT DOCUMENTS

| | | |
|---|---|---|
| DE | 20215659 U1 | 2/2004 |
| FR | 2797886 A | 3/2001 |

(Continued)

OTHER PUBLICATIONS

US 6,465,252, Oct. 15, 2002, Mehmet et al. (withdrawn).

(Continued)

*Primary Examiner* — Manjunath Rao
*Assistant Examiner* — William W Moore
(74) *Attorney, Agent, or Firm* — Miller, Matthias & Hull LLP

(57) ABSTRACT

Methods and compositions provide suitable support material for culturing cells with a desirable metabolic activity. For example, keratinocytes directly grown on flexible supports show metabolic activity. Therapeutic methods and compositions, including wound healing technologies, using the cells grown on flexible supports, wherein the cells exhibit increased metabolic activity are disclosed.

7 Claims, 15 Drawing Sheets

(56) References Cited

U.S. PATENT DOCUMENTS

| | | | |
|---|---|---|---|
| 7,597,712 B2* | 10/2009 | Parenteau et al. | 623/17.11 |
| 7,816,133 B2* | 10/2010 | Gibbs et al. | 435/371 |
| 7,824,913 B2* | 11/2010 | Murphy et al. | 435/371 |
| 7,918,897 B2* | 4/2011 | Bertram et al. | 623/23.65 |
| 8,231,908 B2* | 7/2012 | Kinoshita et al. | 424/582 |
| 2003/0007955 A1 | 1/2003 | Rees et al. | |
| 2004/0049145 A1* | 3/2004 | Flick | 602/41 |
| 2004/0067585 A1 | 4/2004 | Wang et al. | |
| 2005/0178395 A1* | 8/2005 | Hunter et al. | 128/898 |
| 2005/0214259 A1* | 9/2005 | Sano et al. | 424/93.7 |
| 2005/0221486 A1* | 10/2005 | Lin et al. | 435/404 |
| 2006/0018838 A1* | 1/2006 | George et al. | 424/44 |
| 2006/0039896 A1* | 2/2006 | Kleinsek et al. | 424/93.7 |
| 2006/0094114 A1* | 5/2006 | Cook | 435/404 |
| 2006/0153928 A1* | 7/2006 | Kinoshita et al. | 424/582 |
| 2006/0233745 A1* | 10/2006 | Rees et al. | 424/85.1 |
| 2007/0231362 A1* | 10/2007 | Perez et al. | 424/423 |
| 2007/0238167 A1* | 10/2007 | Perez et al. | 435/325 |
| 2008/0108134 A1* | 5/2008 | Murphy et al. | 435/371 |
| 2008/0113007 A1* | 5/2008 | Kurihara et al. | 424/443 |
| 2009/0202654 A1* | 8/2009 | Nixon | 424/574 |
| 2009/0317441 A1* | 12/2009 | Bilbo et al. | 424/423 |

FOREIGN PATENT DOCUMENTS

| | | |
|---|---|---|
| WO | WO 90/00595 A | 1/1990 |
| WO | WO 91/13638 A | 9/1991 |
| WO | WO 99/52356 A | 10/1999 |
| WO | WO 03/035850 A | 5/2003 |

OTHER PUBLICATIONS

International Search Report issued in application No. PCT/US07/82119 (2008).

European office action on application No. 07868529.4 issued on Mar. 15, 2011.

* cited by examiner

I.

II.

DEVICES WITH CELLS CULTURED ON FLEXIBLE SUPPORTS

CROSS-REFERENCE TO RELATED PATENT APPLICATIONS

This application is a U.S. Nationalization of international patent application no. PCT/US2007/082119, filed Oct. 22, 2007, which claims priority to provisional application Nos. 60/862,355, filed Oct. 20, 2006, and 60/943,916, filed Jun. 14, 2007. The disclosures set forth in the referenced applications are incorporated herein by reference in their entireties.

BACKGROUND

Methods and compositions are described for culturing and improving metabolic activity of cells on flexible supports.

Cultured cells and cells grown on solid supports are useful for a variety of in vitro and in vivo tissue engineering purposes, including wound healing. Scaffolds seeded with cultured cells are used for tissue regeneration and repair. Maintaining high metabolic activity of cultured cells is desirable to develop tools and devices for tissue repair. Metabolically active cultured cells are useful in a variety of applications including tissue repair and tissue regeneration.

Although there are many methods and compositions available to promote wound healing, including wound dressings, some wounds do not heal satisfactorily. Treatment of wounds preferably includes wound closure. Some of the wounds that require special care in healing include open cutaneous wounds including burn wounds, neuropathic ulcers, pressure sores, venous stasis ulcers, and diabetic ulcers. Wound healing is generally perturbed/impaired when one or more of the wound healing processes are affected.

Some of the conventional wound dressings include moist occlusive dressings, dry non-occlusive dressings, polyurethane films, colloidal particles, hydrogels, foams and alginates. However, the difficult-to-heal wounds such as diabetic ulcers and pressure sores do not heal timely and properly with the use of such conventional dressings.

Some of the devices for enhancing the healing of wounds, especially chronic wounds (e.g., diabetic wounds), use adherent cells such as keratinocytes grown on a transplantable solid support (e.g., microcarriers such as collagen-coated beads, plastic chips) in an enclosure such as a bag. The cell-coated solid support (e.g., beads) is placed in a biocompatible enclosure, and the solid support along with the enclosure is placed on the wounds. However, the beads may create friction and may deleteriously affect efficient wound healing. The beads may also restrict the amount of keratinocytes that can be applied on wounds to promote effective healing of wounds.

Materials and methods that support growth and functionality of cells, capable of being mass produced, and capable of being used for tissue engineering purposes would be useful.

SUMMARY

Methods and compositions for culturing of cells such as, for example, keratinocytes on flexible supports are provided. Metabolic activity of cells such as keratinocytes may also be increased. Flexible supports are suitable for growth of a variety of cells including endothelial cells, fibroblasts, muscle cells, stem cells, and keratinocytes. Methods and compositions provided herein provide improved wound healing characteristics, ease of application on a target site, and usable for a variety of tissue engineering purposes.

Wound healing methods and compositions using keratinocytes or fibroblasts or a combination thereof grown on flexible supports, wherein the cells exhibit increased metabolic activity are disclosed. For example, cells such as keratinocytes are grown directly on a flexible support such as an enclosure made of high density polyethylene on one side and ethylene vinyl acetate on the other side. Keratinocytes grown on a flexible support made of high density polyethylene and ethylene vinyl acetate exhibited increased metabolic activity as compared to keratinocytes grown on other solid supports for example, porous beads in an enclosure.

A method of culturing cells grown on flexible supports includes:

(a) providing a flexible support material capable of providing a biocompatible surface for cellular growth; and (b) growing cells directly on the surface of the flexible support material and providing a nutrient media.

In an aspect, the metabolic activity of the cells grown on flexible support material is increased.

Suitable flexible support material includes an apertured film, high densitypolyethylene (HDPE), ethylene vinyl acetate (EVA). High Densitypolyethylene (HDPE) and ethylene vinyl acetate (EVA) may be a dual layer, wherein the EVA is on the inside surface that supports the growth of the cells and the HDPE layer is on the outside. Alternately, the HDPE layer is on the inside surface that supports the growth of the cells and the EVA layer is on the outside.

Suitable flexible support material has a plurality of pores of about 0.1 µm to about 1.0 µm in diameter, or 0.4 µm in diameter.

Suitable cells to grow on the support material include for example, keratinocytes, fibroblasts, endothelial cells, smooth muscle cells and stem cells.

The flexible support material may be coated with a biological polymer compound and/or associated with a growth promoting compound. The flexible support material is capable of being directly applied on to a wound surface.

Cells are seeded on to the flexible support material at a density of, for example, about $10^2$ cells to about $10^7$ cells per support material.

A method of engineering a biological tissue, includes:

(a) providing a flexible support material (e.g., an apertured film) capable of providing a biocompatible surface for cellular growth;

(b) culturing cells directly on the surface of the flexible support material and providing a nutrient media; and (c) engineering a tissue from the cultured cells.

A method of repairing a biological tissue in vivo, includes:

(a) providing a flexible support material capable of providing a biocompatible surface for cellular growth;

(b) culturing cells directly on the surface of the flexible support material by providing a nutrient media; and (c) applying the cultured cells to an injured tissue site to repair the tissue.

A method of healing a wound includes:

(a) providing a flexible support material comprising a Delnet™ (apertured film) material;

(b) growing keratinocytes directly on the Delnet™ (apertured film) material; and (c) applying the Delnet™ (apertured film) material with the keratinocytes on the wound.

A wound healing device includes a flexible support material providing a biocompatible surface for cellular growth, wherein the support material includes a population of keratinocytes cultured directly on the support material.

A flexible support material includes a component selected from high densitypolyethylene (HDPE) and ethylene vinyl acetate (EVA) and may have a plurality of pores that range in diameter from about 0.1 μm to about 1.0 μm.

A biocompatible scaffold is seeded with cells cultured on flexible support, wherein the flexible support includes a component selected from high density polyethylene (HDPE) and ethylene vinyl acetate (EVA). A suitable flexible support material is a Delnet™ (apertured film) bag.

DETAILED DESCRIPTION

Figure 1:
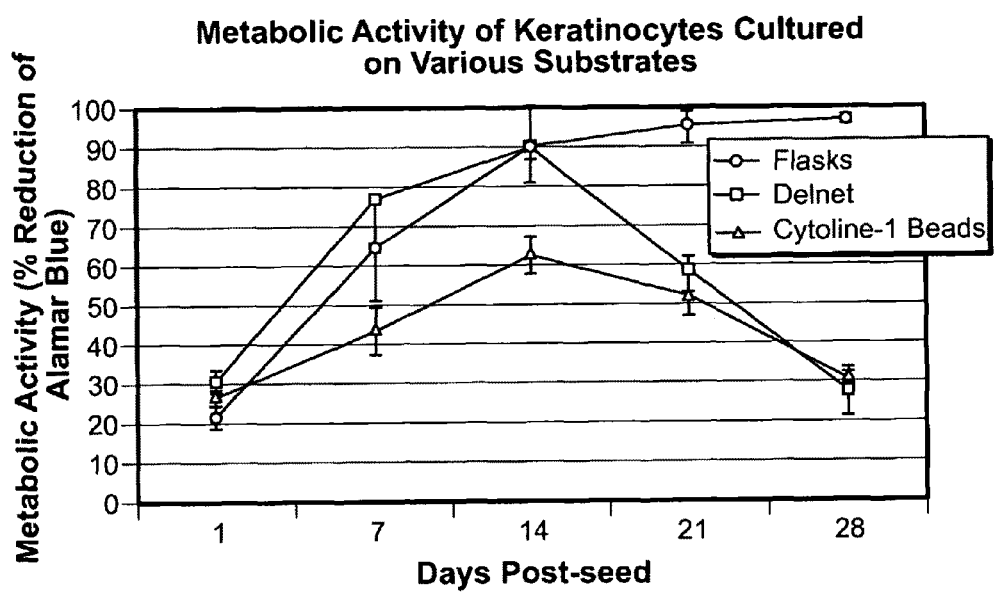
FIG. 1 shows metabolic activity of keratinocytes cultured on various substrates that included cytoline-1 microcarriers, tissue culture flasks, and Delnet™ (apertured film) material.

Methods and compositions to culture a variety of cells including keratinocytes on flexible support material are disclosed. Many cell types, including keratinocytes were cultured directly on flexible supports. Suitable supports were constructed of high density polyethylene (HDPE) and ethylene vinyl acetate (EVA). For example, keratinocyte cells grown on the flexible support material had higher metabolic activity than the cells grown on solid supports such as beads (FIG. 1).

Cultured keratinocytes on flexible support material with higher metabolic activity when compared to cells with lower metabolic activity can be correlated with increased in vivo efficacy for wound healing.

One of the features of the methods disclosed herein is the ability of the cells to be cultured directly on the flexible support material versus merely using the support material as enclosures. For example, cells are cultured directly on Delnet™ (apertured film) bags and are useful for a variety of tissue engineering purposes including wound healing.

Figure 15A:
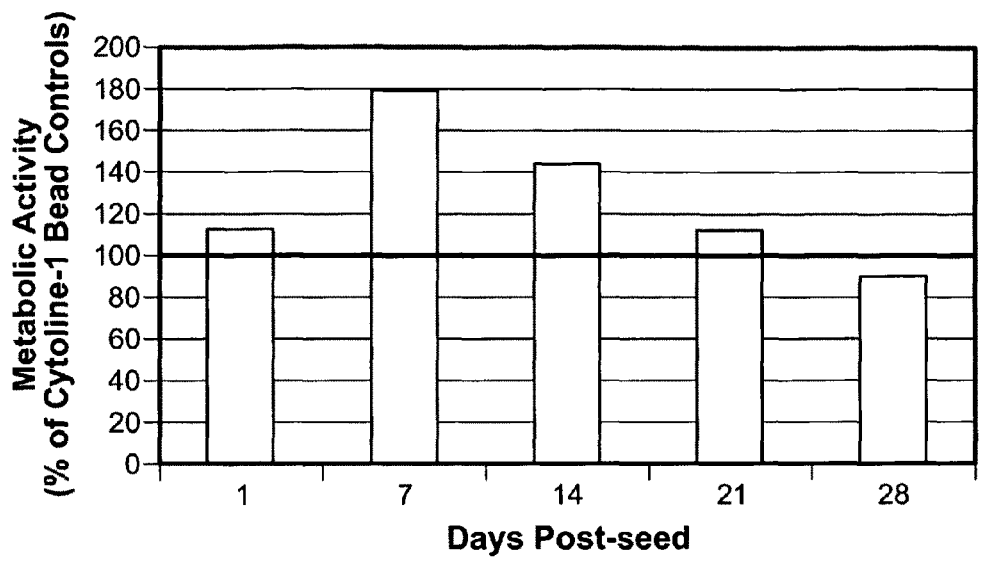
FIG. 15 demonstrates increased metabolic activity of keratinocytes cultured on Delnet™ (apertured film) material compared to controls, which are keratinocytes cultured on Cytoline-1™ beads (A) and comparison of keratinocytes grown on a flexible support material treated with a biopolymer versus an untreated control (B).

Data provided herein demonstrate that the Delnet™ (apertured film) bags also supported the growth and metabolic activity of cells including fibroblasts and aortic endothelial cells. The fibroblasts growing on the Delnet™ (apertured film) material formed a skin-like structure. Cells cultured on Delnet™ (apertured film) material were cryopreserved and were found to possess viability and metabolic activity after the cryopreservation process. The direct cryopreservation of cells cultured on Delnet™ (apertured film) material are useful for long-term storage and transport of cultured Delnet™ (apertured film) material that can be directly used as for example, bandages in wound healing at a clinical site or at the field level. Quantitative comparisons of metabolic activity and/or viability compared to controls e.g., as percent increase are shown in FIG. 15.

The term "flexible support material" refers to a film-like material that is capable of bending, stretching, and providing a biocompatible growth surface for culturing cells.

The term "metabolic activity" is a measure of viability and functionality exhibited by cells grown on a suitable medium with appropriate nutrients. For example, keratinocytes cultured on an apertured film grow and are capable of forming colonies and fibroblasts multiply and are capable of forming a skin-like structure.

Suitable flexible supports include for example, Delnet™ (apertured film) bags made by DelStar Technologies (Middletown, Del.). According to manufacturer's specifications, the bulk of the net includes high density polyethylene (HDPE) (melting point 132° C.) and the skin or adhesive layer is made of ethylene vinyl acetate (EVA)/LLDPE. The EVA has a melting point of 90° C. and the LLDPE has a melting point of 124° C. Based upon the blend ratio, the melting point of the skin is about 110° C. The slick side is HDPE and the stickier side is EVA. The smooth or flat side is the EVA layer and the embossed or raised side is HDPE. In an embodiment, the EVA side is the inside of the bag and the HDPE is the outside surface of the bag.

Delnet™ (apertured film) EP P530Nat-E is made from HDPE with an EVA skin layer to enable easier bonding. All components of P530Nat-E comply with 21CFR177.1520 and 21CFR177.1330 and other regulations concerning the use of plastics in food contact applications. This grade is also available with a white (WHT) and brown (BRN) additive package. FDA approved colors include brown, yellow, blue, white, and natural.

TABLE 1

Properties of a suitable flexible support material (e.g., Delnet ™ (apertured film) bag).

| Properties | Target |
|---|---|
| Basis weight | 0.55 oz/yd$^2$ |
| Thickness | 4.3 mils |
| MD boss ct | 22 per inch |
| CD boss ct | 35 per inch |
| Porosity | 700 cfm/ft$^2$ |
| MD tensile | 5.4 lbs/in |
| Soft pt(skin) | 105° C. |
| Processing range | >123° C. |

The pores in a Delnet™ (apertured film) bag described above are generally triangular shape with an average height of 0.0267 inches and base of 0.0168 inches. The average DelNet™ (apertured film) material may have 35% open area (pores) up to 60% open area.

Delnet™ (apertured film) bags were used for the purpose of demonstrating that flexible support materials with pores enable growth of cultured cells with desirable metabolic activity. Any flexible support material that shares similar functional and structural qualities such as the DelNet™ material is suitable for directly culturing cells, including keratinocytes. Some of the advantages of the configurations disclosed herein include direct culturing of cells on to a flexible support that can be applied as a band-aid (bandage); thereby eliminating the need for a separate solid support such as beads in an enclosure; higher metabolic activity of cultured cells; better shelf life of cultured cells and an increased supply of highly active cells for healing purposes.

The flexible material may include pores. In some aspects, the pores are large enough to permit cultured cells on the flexible support material to cross the flexible support material on to a site of interest, for example, wounds during wound healing. In other aspects, the cells themselves do not cross the flexible material, but the growth factors and other secretions from the cells cross the flexible support material in to a site of interest. In other aspects, only a percent of cells cross the flexible support material, for example about 1-5%, about 5-10% of the cultured cells may pass through the pores to reach the target site.

Flexible support material has pores ranging in size from about 0.1 micron to about 1 micron. The pores may also range in size from about 1 micron to about 10 microns. The pores may range in size from about 0.1 micron to about 0.5 micron. The pores may have a pore size of about 0.4 micron in diameter. All the pores in the flexible support material need not be of the same size or shape. The presence of absence of pores may depend on the nature of the cell type being cultured and also may depend on the nature of the application. For example, keratinocytes grow on flexible support material that has an average pore size of 0.4 microns. Larger pore sizes are also contemplated, for example, about 10 microns to about 100 and to about 500 microns. In some aspects, the flexible support material is selected from polyester, nylon, or polyethylene. For example, the pore size can vary from about 0.1 time the size of a cell of interest (e.g., keratinocytes, fibroblasts or any suitable cell) to about 10 times or 20 times or 50 times or 100 times the size of the cell of interest.

The attachment or avidity of the cells to the flexible support material may be controlled by coating the cell growing surface of the flexible material with one or more biocompatible material that affects the cell attachment properties. In addition, the cell attachment properties are altered by varying the composition of the flexible support material.

Any cell that is culturable is suitable for use to be cultured on the flexible support materials disclosed herein. The cells include fibroblasts, keratinocytes, endothelial cells, melanocytes, smooth muscles cells, macrophages, epithelial cells, stem cells (e.g., adult stem cells, embryonic stem cells), and combinations thereof. In an aspect, the cells to be cultured are derived from the subject that needs to be treated to avoid or minimize adverse immunological reactions.

Tissue engineering uses a combination of cells, for example, cultured cells as disclosed herein, engineering and materials methods, and suitable biochemical and physiochemical factors to improve or replace biological functions. Generally, tissue engineering relates to applications that repair or replace portions of or whole tissues (i.e., for example, skin, bone, cartilage, blood vessels, and bladder). Often, the tissues involved require certain mechanical and structural properties for proper function.

Cells cultured according to the methods described herein are used for wound healing purposes, for example, cultured keratinocytes are used to treat diabetic foot ulcers, venous stasis ulcers, excision wounds, burns, scrapes.

Cells cultured according to the methods described herein are also useful for cosmetics, for example, treatment post skin peel or derm-abrasion, and scar reduction for skin cancer removal, tattoo removal, and for other plastic surgical procedures that require tissue implantation.

Cells cultured according to the methods described herein are used for cardiovascular treatments. For example, preparation of an organotypic blood vessels use cultured smooth muscle cells, endothelial cells and fibroblasts. Cultured heart muscle cells are delivered to damaged heart tissue and cultured smooth muscle cells are delivered to damaged blood vessels.

Flexible support material along with cultured cells are useful in cell encapsulation technology; for example, flexible support material, such as Delnet™ (apertured film) bags with small enough pores to prevent cultured cells from escaping and immune cells from entering, but capable of allowing exchange of nutrients and cellular factors. This encapsulated cells are deliverable to an area of interest that needs treatment.

The flexible support material along with the cultured cells is useful for tissue support and repair, for example by including a cellular component and/or a strong structural support component. Cells are delivered to damaged bone or cartilage to facilitate repair, for reconstructive surgery of muscle and tendons, for tissue support following mastopexy, for tissue support following major liposuction surgery, and hernia repair. Delivery of skeletal muscle or fibroblast cells as part of the flexible support material aids in tissue repair and also provides structural support in the hernia repair process.

Cells cultured according to the methods described herein are useful for oral surgeries to facilitate healing.

The flexible support material, for example, Delnet™ (apertured film) bags are useful, as a support for culture or expansion of adherent cells in-vitro for transwell applications, culture flasks and dishes, as microcarriers for suspension cultures of adherent cells, as hollow fiber bioreactors, and for other extracorporeal clinical uses, such as for example, dialysis-like treatment for exchange of materials between various cell types and the blood stream.

Metabolic activity of cells can be measured by any suitable assay, for example using the Alamar Blue reduction assay. A redox indicator Alamar blue (AB) is used in the Alamar Blue assay, which is a simple, one-step procedure, amenable to high throughput, whereby metabolic activity results in the chemical reduction of AB. Alamar blue is reduced by $FMNH_2$, $FADH_2$, NADH, NADPH, and the cytochromes. Alamar blue both fluoresces and changes color in response to chemical reduction, and the extent of the conversion is a reflection of cell viability or metabolic activity. However, any assay for measuring metabolic activity of cells is suitable. For example, an electrochemical method for measuring metabolic activity and counting cells is described in Kuznetsov (2006).

The term "flexible support material" refers herein to a bendable, pliable, film-like, non-rigid substrate that may or may not contain pores or apertures, is capable of being adapted to a desired shape and is suitable for direct culturing of cells. Suitable flexible support materials include for example, Delnet™ (apertured film) EP P530Nat-E, made from HDPE with an EVA coating, available from DelStar Technologies (Middletown, Del.). The flexible support material may include a bag-like structure. The flexible support material may include a woven fabric-like netted structure. Solid substrates such as beads, or microcarriers, or flasks or test tubes are not intended to be considered as flexible support material in this regard. The term "apertured film" refers to a flexible material that contains a plurality of pores and is compatible for direct cellular growth. The apertured film may have one or more layers and the pore size may be uniform or vary within an acceptable range.

The term "dressing" refers to any suitable material applied to a wound for protection, absorbance, drainage, etc in addition to the flexible support material with cultured cells (see e.g., FIG. 19). Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer). The use of dressings impregnated with pharmacological compounds (e.g., antibiotics, anti-tumor compounds) is also contemplated.

The term "passage" as used herein refers to process of removing adherent cells from a solid support usually by enzymatic cleavage of cell surface proteins, followed by a dilution of the cells in suspension and a subsequent attachment of the cells to a fresh solid support. This process may also be referred to as sub-culture. Based on the number of times the cells are sub-cultured from the tissue, a numerical value is assigned. For example, the initial culture from the digested tissue is designated passage 0, which is sometimes referred to as a primary culture. Upon passage, the primary culture cells are transferred to passage 1. The next sub-culture of these cells would be passage 2 and so forth.

The term "seeding density" as used herein refers to the initial number of cells per area of solid support at sub-culture.

Flexible support material seeded with suitable cells may be applied directly on a target surface, e.g., a wound site such that the cells directly touch the wound or it can be applied such that the cells face away from the wound site, such that only the cell-derived factors migrate to the wound. Any mode of application with either the cells directly touching the target site or indirectly migrate off to the target is suitable.

The contents of co-pending provisional application Ser. Nos. 60/862,355, filed Oct. 20, 2006 and 60/943,916, filed Jun. 14, 2007 are incorporated by reference herein.

The following examples are for illustrative purposes only and are not intended to limit the scope of the disclosure.

EXAMPLES

Example 1

Figure 2:
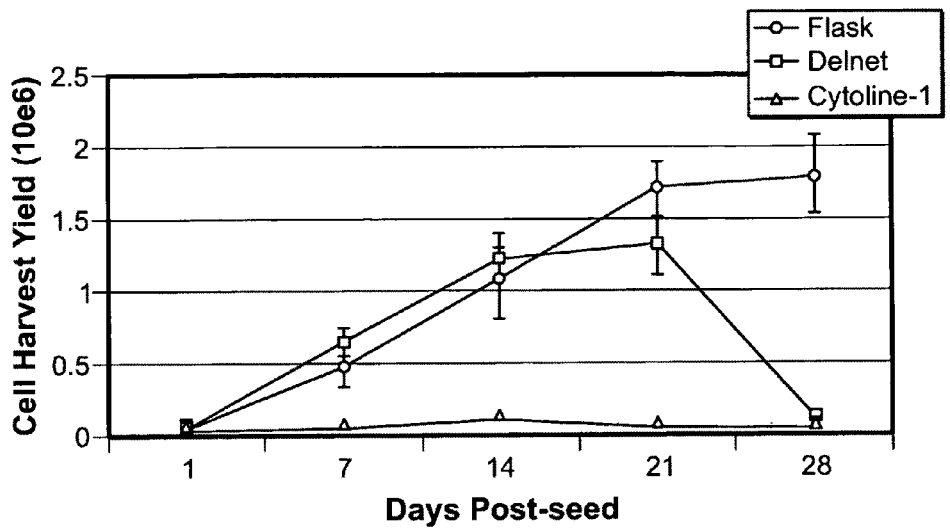
FIG. 2 illustrates the cell harvest yield of keratinocytes from various substrates listed in FIG. 1.
Figure 3:
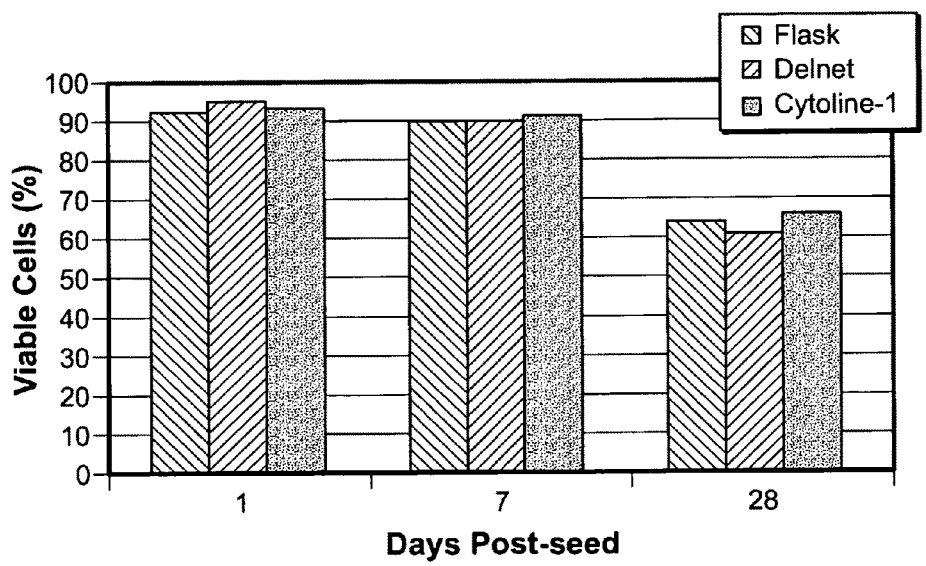
FIG. 3 demonstrates the viability of cells harvested from various substrates listed.

Comparison of Keratinocyte Cultures Initiated on Cytoline-1 Microcarriers, Tissue Culture Flasks, and DelNet™ Material This Example compares keratinocyte growth on three different substrates: tissue culture flasks, Cytoline-1 microcarrier beads, and Delnet™ (apertured film) material, in an animal product-free media system (FIGS. 1, 2, and 3). Each culture is analyzed by measuring metabolic activity and cell viability counts over time post-seeding.

There was some difficulty in determining appropriate trypsin time for each substrate. The trypsinization protocol used in this Example is designed for monolayer cultures on plastic supports. The counts are not highly accurate as many cells were observed to be left behind on the substrates. Therefore, the true cell counts may be somewhat higher than reported herein. The method for counting cells requires that cells are removed from the substrate and counted in suspension. Cells left behind on the substrate are not in suspension and are not counted.

Each substrate was seeded with a cell suspension of different concentration. The purpose of this difference was to standardize the comparison by starting with similar metabolic activity at day 1. The differences at day 1 might be caused by variable attachment to each substrate and by the fact that the beads and the Delnet™ (apertured film) have large pores through which cells can pass and not come in contact with the substrate. Similar starting metabolic activity for each substrate sample was achieved.

Over the first 14 days of culture, the keratinocytes growing on Delnet™ (apertured film) have a similar metabolic activity, cell yield, and cell viability to those growing on tissue culture flasks. Keratinocytes growing on Cytoline-1 beads have a lower metabolic activity over the first 14 days in culture compared to those growing on Delnet™ (apertured film) and tissue culture flasks. After 14 days a decrease in metabolic activity of keratinocytes grown on Delnet™ (apertured film) was observed compared to the keratinocytes grown on flasks. Some cells may be trapped within the porous beads even after the trypsinization procedure.

This decrease in metabolic activity in Delnet™ (apertured film) as compared to the flasks-grown keratinocytes may be because that the cells growing on Delnet™ (apertured film) became confluent faster than those growing on the flask. Keratinocytes generally undergo contact inhibition and begin to slow their growth as they approach confluence. Although approximately the same number of cells was started for each condition, the cells on the flasks were less concentrated than those on the Delnet™ (apertured film). The available surface area is 75 $cm^2$ for the flask, <16 $cm^2$ for the Delnet™ (apertured film) piece that was used, and <32 $cm^2$ for the Cytoline-1 beads. An effort was made to seed the keratinocytes in a concentrated area in the center of the flasks, the cell suspension did spread out over the flask. The cell coverage area on the flasks had spread well beyond the initial seeding, upon microscopic observation.

Therefore, this Example demonstrates that keratinocytes grow well on Delnet™ (apertured film) material when compared to a standard adherent substrate for cell culture—the tissue culture flask. Keratinocytes cultured on Delnet™ (apertured film) reached a higher measurable metabolic activity than keratinocytes cultured on Cytoline-1 beads. It is sometimes difficult to remove the cells from the beads for counting. Some cells are likely residing within the beads based on metabolic activity, yet were unable to be retrieved by trypsinization. It is possible that the cells are caught in the pores of the beads.

Example 2

Growth and Metabolic Activity of Human Dermal Fibroblasts on DelNet™ Material

Figure 4:
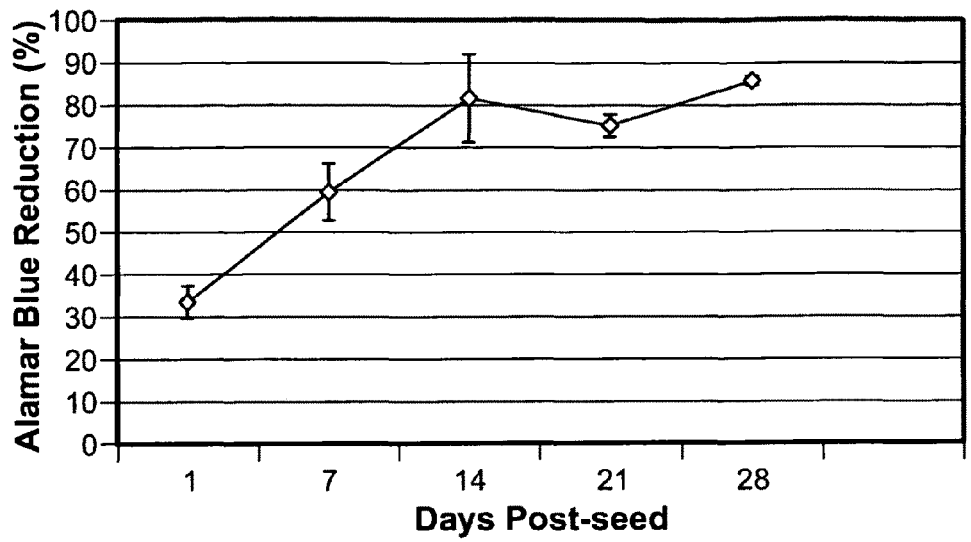
FIG. 4 demonstrates the metabolic activity of normal human fibroblasts on DelNet™.
Figure 5:
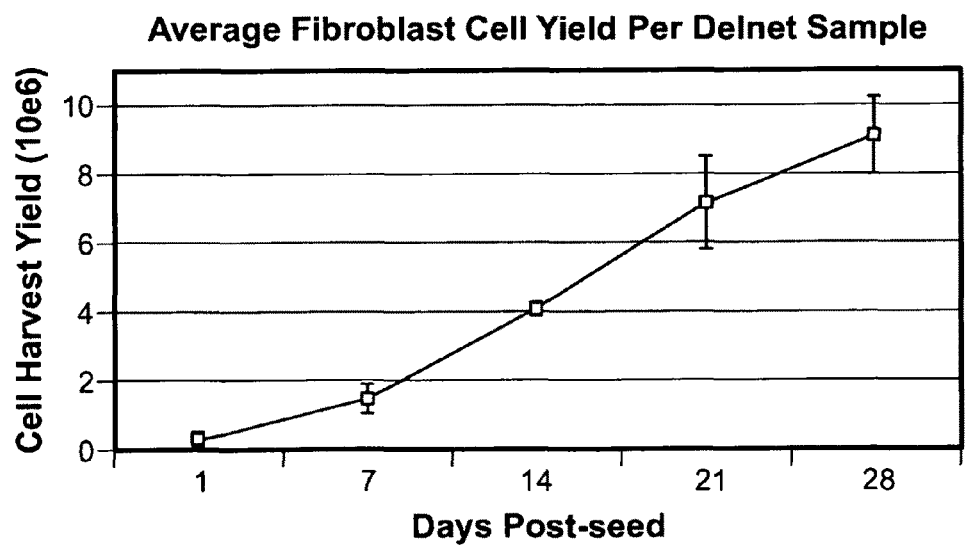
FIG. 5 shows average cell yield of the cultured fibroblasts.
Figure 6:
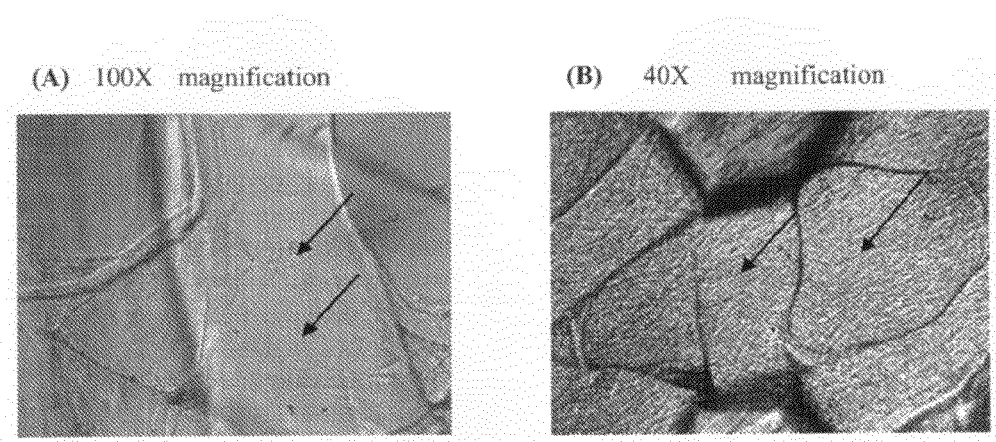
FIG. 6 shows human dermal fibroblasts attached to Delnet™ (apertured film) material at day 1 post-seed at 100× magnification (A) and 14-days post-seed (B) at 40× magnification.
Figure 7:
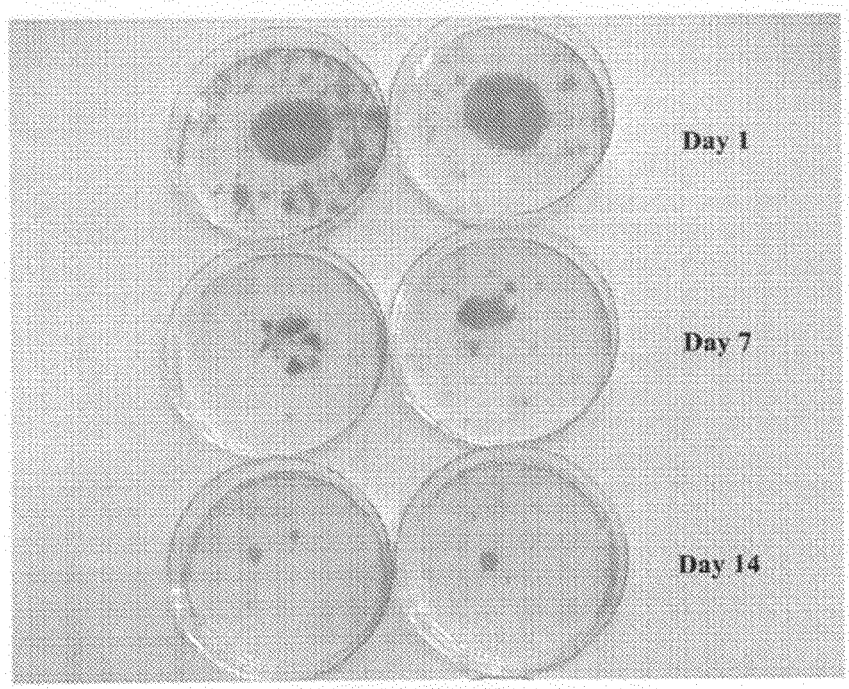
FIG. 7 shows formation of keratinocytes colonies on a secondary surface following migration off an apertured film surface after days 7 and 14 post-seed.

The purpose of this Example was to analyze human fibroblast attachment and growth on Delnet™ (apertured film) material (FIGS. 4, 5, and 6). In addition, comparison of human fibroblast cultures initiated on Cytoline-1 microcarriers vs. human fibroblast cultures initiated on delnet material was performed (FIG. 7). In this Example cultures were analyzed by measuring metabolic activity and cell viability counts over time post-seeding.

The microscopic observations shown in the photographs (FIGS. 6A and 6B) demonstrate proliferative cultures of fibroblasts attached to the Delnet™ (apertured film) material. Within 14 days, the fibroblasts appear to have formed a "skin", which covered the pores of the Delnet™ (apertured film) fabric. This Example shows that human dermal fibroblasts adhered to and proliferated on Delnet™ (apertured film) material. Such cultured fibroblasts are useful in tissue engineering, tissue grafting, tissue repair, tissue transplantation or for any regenerative or therapeutic purpose that requires fibroblasts.

Cultured fibroblasts can give rise to other cells, such as bone cells, fat cells, and smooth muscle cells. Cultured fibroblasts provide a structural framework (stroma) for many tissues, and play an important role in wound healing.

Fibroblast growth on two different substrates—Cytoline-1 Microcarrier Beads, and Delnet™ (apertured film) material—was compared. Metabolic activity over time post-seed was measured.

One vial of cryopreserved human fibroblasts, cell bank lot "HDFn P3-4, $2 \times 10^6$ cells/vial 3-27-06" was thawed and seeded to four T-162 flasks at passage 4. Each flask was cultured with 40 mL of Medium 106 supplemented with LSGS (Cascade Biologics) growth media. Each flask was incubated at 37° C., 5% $CO_2$ with loosened caps. Each flask was fed with 40 mL of Medium 106 supplemented with LSGS growth media every 2-3 days throughout passage 4. The cells were microscopically observed at each feed and the percentage of flask surface confluence was estimated. Once the cells reached approximately 80% confluent, the cells were harvested by trypsinization. This harvest was followed by trypsin neutralization to yield a uniform cell suspension in Medium 106 supplemented with LSGS growth media. The cells were counted in suspension using a hemacytometer to determine the total harvest yield. The cells were passaged to p5 at $1 \times 10^6$ cells per T-162 Flask. The following cell suspensions were prepared from the passage harvest:

| Cell Suspension | Concentration (cells/mL) | Minimum Final Volume (mL) |
|---|---|---|
| A | $1.00 \times 10^6$ | 30 |
| B | $0.35 \times 10^6$ | 32 |
| C | $0.70 \times 10^6$ | 32 |

About thirty 1.5"×1.5" pieces of double layered Delnet™ (apertured film) were placed in 100 mm petri dishes. About 30 mL of Cytoline-1 Microcarriers, prepared according to manufacturer's instructions were added to one T-175 flask. About 30 mL of Cell Suspension "A" was transferred to the 30 mL of microcarrier beads. About 2 mL of Cell Suspension "B" was transferred to each of the 15 pieces of double layered Delnet. Care was undertaken to maintain the entire 2 mL on the Delnet™ film). About 2 mL of Cell Suspension "C" was transferred to each of 15 pieces of double layered Delnet. Care was undertaken to maintain the entire 2 mL on the Delnet™ (apertured film). Each sample was incubated at room temperature for 1 hour. Each piece of double layered Delnet™ (apertured film) was transferred to 150 mL bottles containing 175 mL (filled) of Medium 106 supplemented with LSGS growth media. The caps were sealed and incubated at 37° C. About 2 mL each of the Cytoline-1 Microcarriers was transferred to each of the fifteen 150 mL bottles containing 175 mL (filled) of Medium $10^6$ supplemented with LSGS growth media. The caps were sealed and incubated at 37° C.

The following samples have been prepared (15 samples per condition):

|  | A | B | C |
|---|---|---|---|
| Microcarriers | $2.0 \times 10^6$ | N/A | N/A |
| Delnet | N/A | $0.7 \times 10^6$ | $1.4 \times 10^6$ |

At the following time points post-seed (day 1, 7, 14, 28), the metabolic activity was determined in three samples from each condition. The percentage of alamar blue reduction at each time point for each sample was calculated.

Delnet™ (apertured film) was seeded with cell suspensions of lower concentration than those used for seeding the Cytoline-1 Microcarriers. The purpose of this difference is to standardize the comparison by starting with similar metabolic activity at day 1. The differences at day 1 could be caused by variable attachment to each substrate and by the fact that the beads and the Delnet™ (apertured film) have different sized large pores through which cells can pass and not come in contact with the substrate. Seeding densities used for the two materials did not give a similar day 1 metabolic activity (FIG. 7). The day 1 metabolic activity for the seeding density of cells on beads was higher than those chosen for cells on Delnet™ (apertured film). FIG. 7 demonstrated that the fibroblast cells grow well on the beads and are comparable to fibroblast cells cultured on the Delnet (FIG. 7).

Example 3

Feasibility Study for Culture of Human Aortic Endothelial Cells on DelNet™ Material The purpose of this Example was to analyze human aortic endothelial cell attachment and growth on Delnet™ (apertured film) material. Cultures were analyzed by measuring metabolic activity and cell viability counts over time post-seeding.

Figure 8:
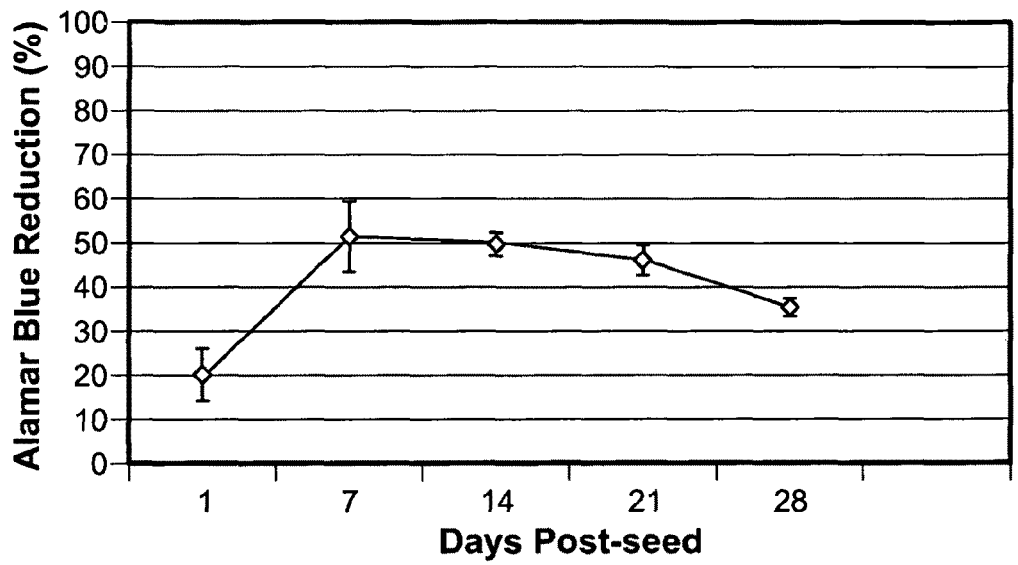
FIG. 8 shows metabolic activity of human aortic endothelial cells cultured on Delnet™ (apertured film) material.
Figure 9:
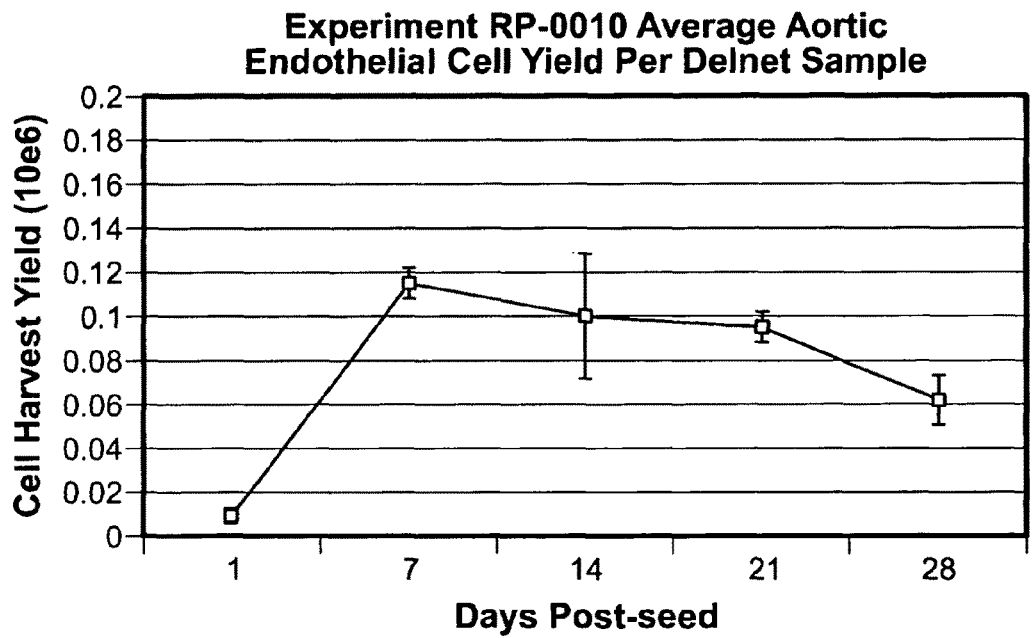
FIG. 9 shows average cell yield of the human aortic endothelial cells cultured on Delnet™ (apertured film) material.
Figure 10:
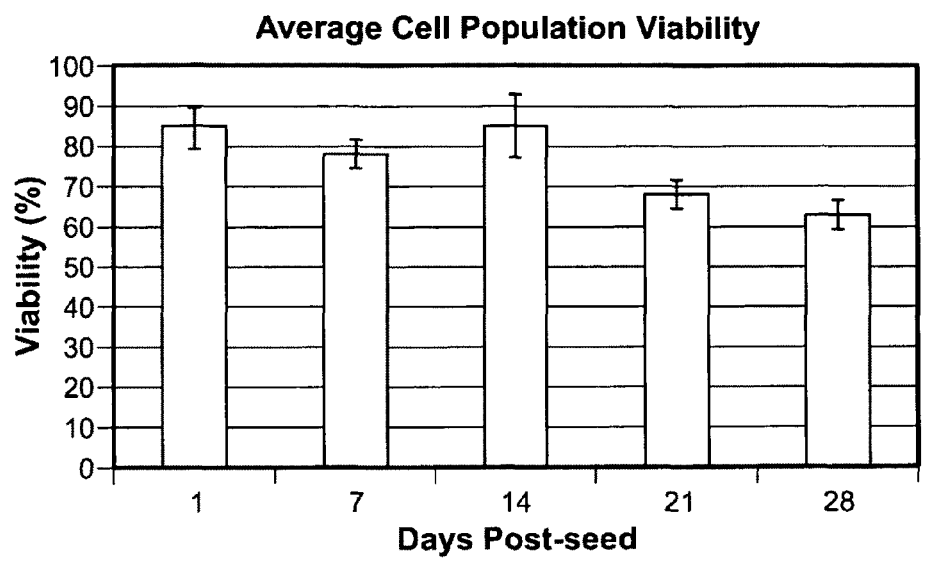
FIG. 10 shows average cell population viability of human aortic endothelial cells cultured on Delnet™ (apertured film) material.

This Example demonstrates that aortic endothelial cells adhere and proliferate on Delnet™ (apertured film) material (FIGS. 8, 9, and 10). This Example showed that Delnet™ (apertured film) material supports growth of aortic endothelial cells for culturing and subsequent applications.

Cryopreserved human aortic endothelial cells, (Cascade Biologics catalogue number C-006-5C) are used to evaluate the potential of aortic endothelial cells to grow on Delnet material or any equivalent flexible support material.

Cultured endothelial cells find numerous applications for example in the repair of endothelial lining, vasculature, and repair of blood vessels due to damage from a variety of agents such as free radicals and atherosclerosis. Cultured endothelial cells with improved metabolic activity as disclosed herein are useful in the design of the scaffolds and other tissue-repair and tissue regenerative products for cardiovascular tissue engineering.

Example 4

Figure 12:
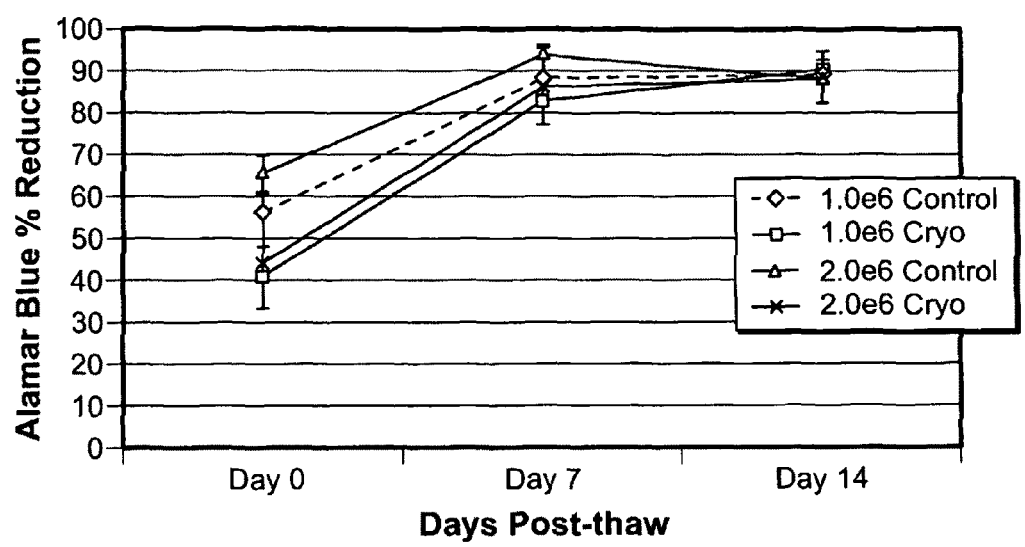
FIG. 12 shows metabolic activity of passage 4 human keratinocytes, comparing two seeding densities and cryopreserved vs. non-cryopreserved cultures on Delnet™ (apertured film) material.

Cryopreservation of Human Keratinocytes Cultured for Two Days on Delnet™ (Apertured Film) Material: Seeding Density Comparison and Recovery Analysis The purpose of this Example was to analyze metabolic activity of human keratinocytes cultured on Delnet™ (apertured film) material and cryopreserved to −80° C. (FIG. 12). Metabolic activity was analyzed over time post-thaw from cryopreservation as compared to non-cryopreserved controls. This example also analyzed two different seeding densities on the DelNet™ material.

Human keratinocyte cultures were obtained at passage 4 on tissue culture flasks, in EpiLife animal product-free medium (Cascade Biologics; Portland, Oreg.). After the cells are approximately 80% confluent, the cells were harvested by trypsinization. Trypsin neutralization was used and a uniform cell suspension was formed in EpiLife Medium. The cells were counted in suspension using a hemacytometer to determine the total harvest yield. The cell suspension was adjusted to yield two solutions, one at $0.5 \times 10^6$ cells/mL and one at $1.0 \times 10^6$ cells/mL in EpiLife medium. Twenty four 1.5"×1.5" pieces of double layered Delnet™ (apertured film) material were placed in each of twenty four 100 mm Petri dishes.

To prepare devices (e.g., keratinocytes seeded to double layer Delnet™ (apertured film) as a wound healing device) seeded with $1.0 \times 10^6$ cells, 2 mL of the $0.5 \times 10^6$ cells/mL cell suspension was transferred to each of the 12 pieces of double layered DelNet™ (apertured film).

Each sample was allowed to sit at room temperature for 1 hour. Each piece of double layered Delnet™ (apertured film) was transferred to appropriately labeled 150 mL bottles containing 175 mL (filled) of EpiLife medium. The caps were sealed and incubated at 37° C. After two days of incubation, 6 devices from each of the two conditions were cryopreserved using a controlled rate freezer.

The bottles containing the devices to be cryopreserved were transferred to a bio-safety cabinet. The media was removed from each bottle containing a device. About 10 mL of chilled (4-6° C.) Synth-a-Freeze solution (Cascade Biologics; Portland, Oreg.) was added to each bottle containing a device and to one bottle containing a 1.5"×1.5" pieces of double layered DelNet™ as the sample temperature probe. Each bottle was sealed and placed immediately in the controlled rate freezer. The sample probe was placed in the container holding the piece of DelNet™ without living cells. The chamber temperature was immediately dropped to 4° C.

After the sample probe reached 5° C., the chamber temperature was ramped at 1° C./min from 4° C. to −40° C., then 2° C./min from −40° C. to −90° C. The chamber was held at −90° C. until it was ready to thaw the samples.

The samples were removed from the controlled rate freezer and transferred immediately to a 37° C. water bath until just thawed. This took approximately 4 minutes. The bottles were then transferred to a bio-safety cabinet.

The Synth-a-Freeze cryoprotectant solution was removed from each device and 50 mL of EpiLife medium was added to rinse. The 50 mL of EpiLife medium was removed and fresh 175 mL of EpiLife medium was added to each bottle. The caps were sealed and incubated at 37° C.

At the following time points post-thaw (day 0, 7, 14), metabolic activity was determined in two samples from each of the four conditions ($1.0 \times 10^6$ cells Control, $1.0 \times 10^6$ cells Cryopreserved, $2.0 \times 10^6$ cells Control, and $2.0 \times 10^6$ cells Cryopreserved). The percentage of alamar blue reduction was calculated at each time point for each sample.

Keratinocytes cultured on Delnet™ (apertured film) material for two days, followed by a controlled rate freeze using a cryoprotectant solution recovered and proliferated. Cryopreservation reduces the metabolic activity of the device as measured on the day of thaw. Over time post-thaw the metabolic activity of the device increases to a level similar to non-frozen controls by day 7.

Example 5

Figure 11:
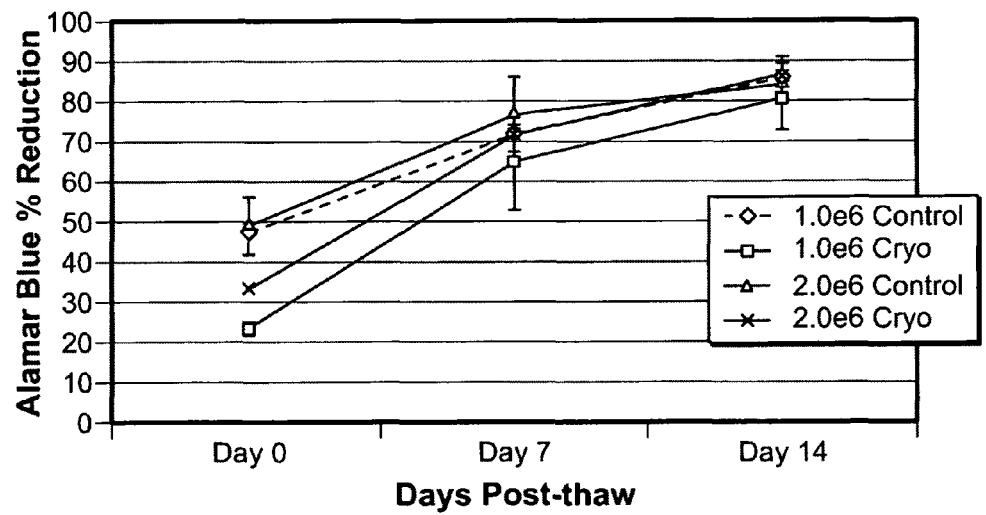
FIG. 11 shows metabolic activity of passage 3 human keratinocytes, comparing two seeding densities and cryopreserved vs. non-cryopreserved cultures on Delnet™ (apertured film) material.

Cryopreservation of Human Keratinocytes Cultured for Two Days on DelNet™ Material: Seeding Density Comparison and Recovery Analysis This purpose of this Example was to analyze metabolic activity of human keratinocytes cultured on Delnet™ (apertured film) material and cryopreserved to −80° C. (FIG. 11). Metabolic activity was measured over time post-thaw from cryopreservation as compared to non-cryopreserved controls. Two different seeding densities on the Delnet™ (apertured film) material were also analyzed.

Human keratinocyte cultures were obtained at passage 3 (compared to passage 4 in Example 4) on tissue culture flasks, in EpiLife animal product-free medium (Cascade Biologics; Portland, Oreg.). After the cells were approximately 80% confluent, the cells were harvested by trypsinization. Trypsin neutralization was used and a uniform cell suspension was formed in EpiLife Medium. The cells were counted in suspension using a hemacytometer to determine the total harvest yield. The cell suspension was adjusted to yield two solutions, one at $0.5 \times 10^6$ cells/mL and one at $1.0 \times 10^6$ cells/mL in EpiLife medium. Twenty four 1.5"×1.5" pieces of double layered Delnet™ (apertured film) material were placed in each of twenty four 100 mm Petri dishes.

To prepare devices seeded with $1.0 \times 10^6$ cells, 2 mL of the $0.5 \times 10^6$ cells/mL cell suspension was transferred to each of the 12 pieces of double layered DelNet™.

To prepare devices seeded with $2.0 \times 10^6$ cells, 2 mL of the $1.0 \times 10^6$ cells/mL cell suspension was transferred to each of 12 pieces of double layered Delnet™ (apertured film). Each sample was allowed to sit at room temperature for 1 hour. Each piece of double layered Delnet™ (apertured film) was transferred to appropriately labeled 150 mL bottles containing 175 mL (filled) of EpiLife medium. The caps were sealed and incubated at 37° C. After two days of incubation, 6 devices from each of the two conditions were cryopreserved using a controlled rate freezer.

The bottles containing the devices to be cryopreserved were transferred to a bio-safety cabinet. The media was removed from each bottle containing a device. About 10 mL of chilled (4-6° C.) Synth-a-Freeze solution (Cascade Biologics; Portland, Oreg.) was added to each bottle containing a device and to one bottle containing a 1.5"×1.5" pieces of double layered DelNet™ as the sample temperature probe. Each bottle was sealed and placed immediately in the controlled rate freezer. The sample probe was placed in the container holding the piece of DelNet™ without living cells. The chamber temperature was immediately dropped to 4° C.

After the sample probe reaches 5° C., the chamber temperature was ramped at 1° C./min from 4° C. to −40° C., then 2° C./min from −40° C. to −90° C. The chamber was held at −90° C. until it was ready to thaw the samples.

The samples were removed from the controlled rate freezer and transferred immediately to a 37° C. water bath until just thawed. This takes approximately 4 minutes. The bottles were then transferred to a bio-safety cabinet.

The Synth-a-Freeze cryoprotectant solution was removed from each device and 50 mL of EpiLife medium was added to rinse. The 50 mL of EpiLife medium was removed and fresh 175 mL of EpiLife medium was added to each bottle. The caps were sealed and incubated at 37° C.

At the following time points post-thaw (day 0, 7, 14), metabolic activity was determined in two samples from each of the four conditions (1.0×10$^6$ cells Control, 1.0×10$^6$ cells Cryopreserved, 2.0×10$^6$ cells Control, and 2.0×10$^6$ cells Cryopreserved).

The percentage of alamar blue reduction was calculated at each time point for each sample. Keratinocytes obtained at passage 3, cultured on Delnet™ (apertured film) material for two days, followed by a controlled rate freeze using a cryoprotectant solution, recovered and proliferated. Cryopreservation reduces the metabolic activity of the device as measured on the day of thaw. Over time post-thaw the metabolic activity of the device increases to a level similar to non-frozen controls by day 7.

Figure 13A:
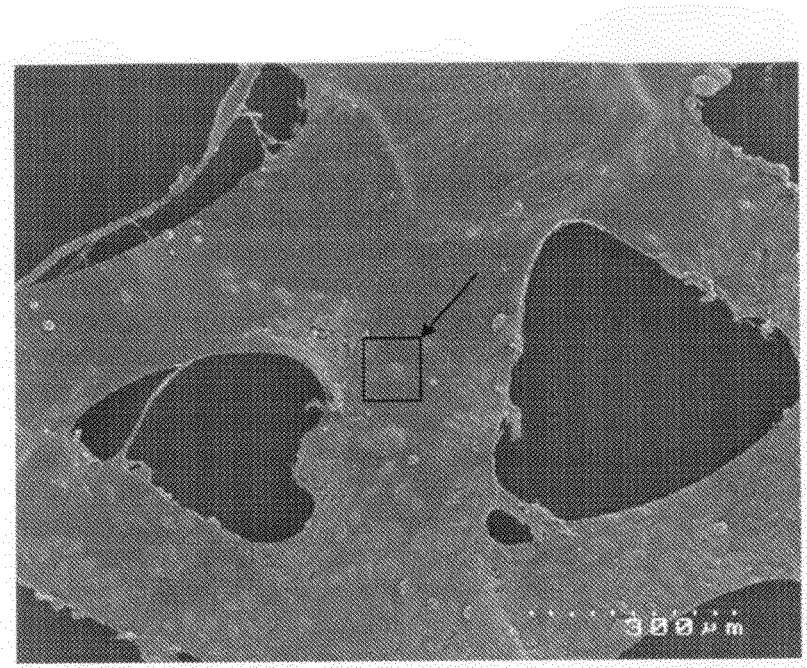
FIG. 13 shows a scanning electron photomicrograph of human keratinocytes cultured on Delnet™ (apertured film) material (A). A single attached cell is highlighted (surrounded by a box) and magnified in (B)—scanning electron photomicrograph of a single keratinocyte (highlighted in A) attached to Delnet™ (apertured film) material. The arrows identify specific areas of focal attachment of the cell to the material.
Figure 13B:
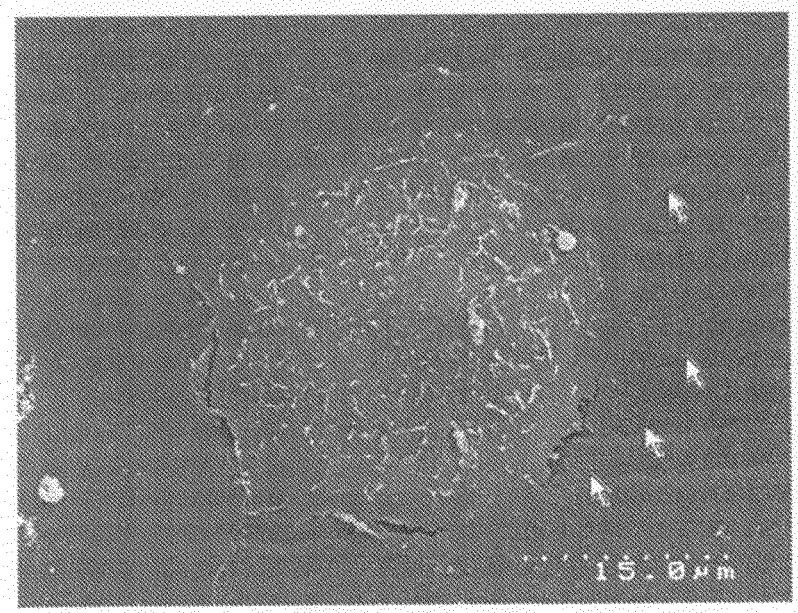

Scanning electron photomicrographs of human keratinocytes cultured on Delnet™ (apertured film) material are shown on FIG. 13 (A-B). A single attached cell is highlighted (surrounded by a box) and magnified in (FIG. 13B)—scanning electron photomicrograph of a single keratinocyte (highlighted in A) attached to Delnet™ (apertured film) material. The arrows identify specific areas of focal attachment of the cell to the material.

Example 6

Configurations Using the Flexible Solid Supports for Wound Healing

Figure 18A:
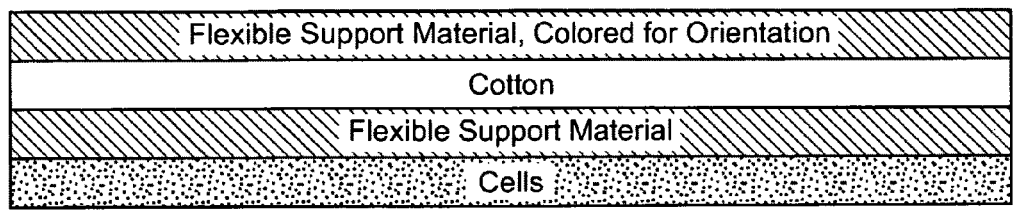
FIG. 18 shows different schematic illustrations of a flexible solid material used in the band-aid-like (bandage) configurations.
Figure 18B:
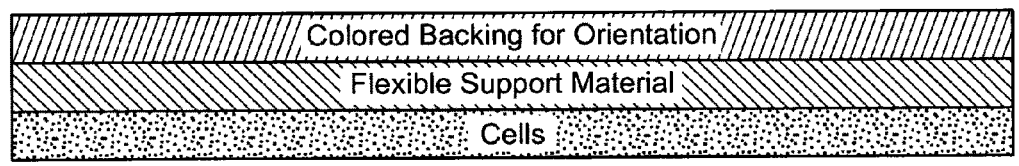
Figure 18C:
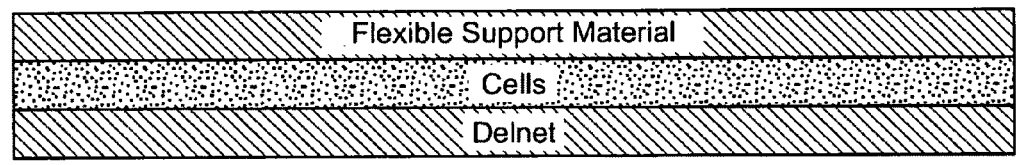

FIG. 18 illustrates several configurations involving band-aid-like (bandage) structures. For example, FIG. 18A illustrates a standard band-aid configuration involving the novel use of cells grown directly on the flexible support material such as a Delnet™ (apertured film) bag. FIG. 18B illustrates a swatch configuration and FIG. 18C illustrates a bag configuration. In the band-aid configuration, two Delnet™ (apertured film) layers are sandwiched by a cotton support and the cells are grown directly on the inner Delnet™ (apertured film) layer and applied directly to the wound surface. In the swatch configuration, Cells are grown on side of the Delnet™ (apertured film) bag and the other side of the Delnet™ (apertured film) material is backed by a color-coded support for orientation purposes. The Delnet™ (apertured film) material itself can also be color coded eliminating a separate color-coded support. In the bag configuration, two Delnet™ (apertured film) layers enclose the cells grown directly on the Delnet™ (apertured film) bags and applied directly on the wound surfaces for healing.

FIG. 19 illustrates several embodiments of wound dressings envisioned with the compositions disclosed herein. In FIG. 19A, coded scheme for the device is shown. In the embodiment illustrated in FIG. 19B, the flexible solid material (e.g., Delnet™ (apertured film) bag) is placed directly on the wound and a wound dressing is placed on top of the bag. The bag is left in place for several days.

Figure 19A:
FIG. 19 shows different schematic illustrations for the use of a flexible support material (e.g., Delnet™ (apertured film) bag).
Figure 19B:
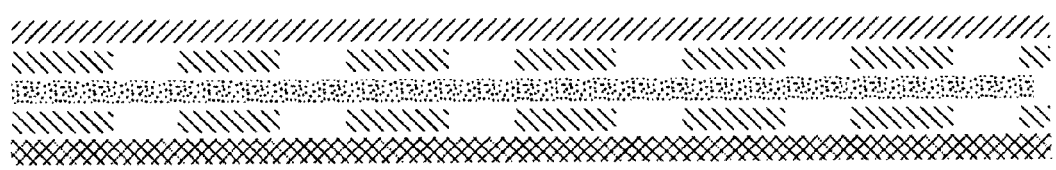
Figure 19C:
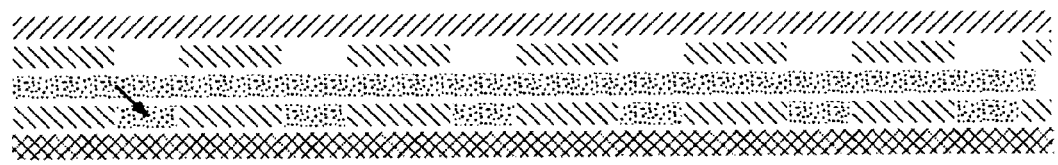
Figure 19D:
Figure 19E:

In FIG. 19C, the cells (e.g., keratinocytes) migrate off of the bag, through the pores in the bag and onto the wound bed. In FIG. 19D, the bag is removed, leaving islands of cells behind. This process may be repeated. In FIG. 19E, the islands of cells expand to cover the wound. Additionally, the cells that are attached to the Delnet™ (apertured film) and migrating onto the wound bed provide wound healing growth factors and cytokines.

Any suitable flexible support material that shares similar functional and structural qualities such as the Delnet™ (apertured film) material is used for directly culturing cells, including keratinocytes. Some of the advantages of the configurations disclosed herein include direct culturing of cells on to a flexible support that can be applied as a band-aid (bandage); eliminating the need for a separate support such as the beads in a bag; higher metabolic activity of cultured cells; better shelf life of cultured cells and an increased supply of highly active cells for healing purposes.

Example 7

Tissue Engineering Applications

One of the goals in tissue engineering is to grow a tissue or organ that is targeted rather than replace that tissue or organ with a prosthetic device. In many aspects, the cellular materials used may be human derived from a source, and preferably from the patient. Typically, the suitable cells derived from the patient or otherwise are seeded onto a substrate or a matrix support and are allowed to proliferate until an adequate amount of tissue or cells are available for transplantation to the patient. The ensuing tissue-grown substrate is classified as a "device" and is generally subject to a regulatory agency approval.

In vitro and in vivo models are often used to evaluate the safety or compatibility of the cellular material. The substrate or matrix materials used to "seed" the cellular materials are subjected to routine device evaluations. These products are sometimes considered as implants that degrade. In some aspects, the substrate or matrix or a protective polymer is considered a permanent implant that allows the cells to function without immune rejection. Some of the factors that are considered in choosing a suitable substrate or support material is biocompatibility, cytotoxicity, sensitization or allergenicity and mutagenicity (genotoxicity).

For example, any substrate material can be coated or in any way associated with the Delnet™ (apertured film) material such that the cells are grown directly on the Delnet™ (apertured film) material. This ensures increased metabolic activity and desired cell density for tissue engineering applications.

Delnet™ (apertured film) material may be used as a solid support for tissue engineering in a similar manner as, for example, Corning-Costar's Trans-Well™ inserts. The Delnet™ (apertured film) provides flexible support for adherent or non-adherent cells in three dimensional cultures, while allowing for media exchange between all sides of the tissue construct. For example the Delnet™ (apertured film) in a Trans-Well™ configuration is useful for production of bioengineered skin. The dermal layer including dermal cells within a lattice of collagen and other matrix molecules is attached to the DelNet™ support. The epidermal layer that includes differentiated keratinocytes is formed on top of the dermal layer, giving an organotypic skin construct. The engineered skin construct is suspended on the Delnet™ (apertured film) in a nutrient rich media, allowing for nutrient exchange both above and below the engineered tissue. A tissue engineering use for cells on DelNet™ is for production of an engineered blood vessel. In this case vascular smooth muscle cells are cultured on DelNet™ to form a confluent sheet. Following smooth muscle formation vascular endothelial cells are cultured on top of the smooth muscle to form a differentiated endothelial layer. The entire construct is rolled to form a vascular shape. Conversely, the vascular shape may be pre-formed from the DelNet™ prior to initiation of tissue culture.

Example 8

In-Vivo Wound Healing Using a Diabetic Rat Model

This example demonstrates the efficacy of a wound healing device in a pre-clinical mouse model. Efficacy of a flexible support material (e.g., Delnet™ (apertured film)) seeded with human epidermal keratinocytes (HEK) was used as a bioactive wound healing device.

Male nude athymic rats, aged 8-10 weeks, were selected as the animal model. The experiments includes the following testing conditions:

Group 1, Normoglycemic, Control: Normoglycemic rats with 8 mm dermal punch full-thickness skin defect on the dorsum, caudal to the scapulae, treated with Delnet™ (apertured film) material alone.

Group 2, Hyperglycemic, Test: Streptozotocin (STZ)-induced diabetic rats with 8 mm dermal punch full-thickness skin defect on the dorsum, caudal to the scapulae, treated with HEK-loaded Delnet™ (apertured film) material.

Group 3, Hyperglycemic, Control: STZ-induced diabetic rats with 8 mm dermal punch full-thickness skin defect on the dorsum, caudal to the scapulae, treated with Delnet™ (apertured film).

Body weights were measured on Day 0, 6 and 10 for all animals enrolled in the study. Diabetes was induced in 18 rats (70 mg/kg streptozotocin IP, in 0.2 ml 10 mM citrate pH5.5) following an overnight fast. 14 of these rats were enrolled in Groups 2 and 3. A total of 21 male rats were enrolled in this study, including: 14 acute diabetic WAG nude rats and 7 non diabetic WAG nude controls. Rats were singularly housed in 3 isolators exclusive to the study. All rats were maintained under strict pathogen-free conditions and were minimally handled. Drinking water containing antibiotic and standard chow were provided ad libitum. Transgel or mush was supplied to diabetic animals that were dehydrated. Rats were exposed to a 12-hr light/dark light cycle (on @ 6 AM; off @ 6 PM). All animals were maintained in accordance with standards established by the National Research Council.

Clinical Care: Diabetic rats were maintained using an optimized insulin treatment protocol. Each diabetic rat received a single daily dose of exogenous insulin (PZI) administered between 12-1 PM, daily. To establish a dose that would maintain hyperglycemia but not lead to fatality, a dose of 0.5 Units PZI was administered beginning on Day 2. The ideal insulin dose should result in target serum glucose of 350-500 mg/dL, 241 hr post insulin treatment. If blood glucose was >500 mg/dL the PZI dose was increased incrementally until a blood glucose between 300-500 mg/dL was reached. The dose on this day was considered the target dose. The target dose for each animal was managed to maintain a hyperglycemic but non-ketoacidotic state. Fluid therapy (saline and/or lactated Ringer's) was administered as necessary to maintain hydration and regulate ketoacidosis. Glucose homeostasis was monitored daily by urine testing method (Clinistix, Bayer). Rats with 4+ glucose levels were tested for ketones in urine (Ketostiks, Bayer).

Human epidermal keratinocytes (HEK)-loaded Delnet™ (apertured film) was prepared according to the methods disclosed herein. Devices containing human keratinocytes were supplied in a small sterile container and stored in medium at 37° C. at BRM's. Control devices without keratinocytes were kept in a sterile environment.

Rats were sorted into 3 treatment groups. Group 1 consisted of 7 non-diabetic rats. Streptozotocin-induced diabetic rats were enrolled into Group 2 and 3 based on their blood glucose levels.

Rats were anesthesized with ketamine/zylazine for the surgical procedure. The area to be excised was cleansed with Betadine and a topical anesthetic (EMLA Cream) was used to numb the excision area. An 8 mm punch was used to remove a full thickness plug of skin from the dorsal region of each rat. Devices were placed over the wound followed by Band Aids and Vetrap. The animals were then placed on a heating pad until recovered.

Several days after STZ administration, all the animals in all three groups were treated as follows: After administering anesthesia, 8 mm full-thickness skin defect was created with sterile dermal punch; Delnet™ (apertured film) material was applied to the wound (trimmed to slightly overlap the wound margins) and the wound site was covered with a self-adhesive bandage. The bandage was then covered with protective, non-occlusive wrap. The animals in groups 1 and 3 received bare DelNet material and the animals in group 2 receive HEK-loaded Delnet™ (apertured film) material.

After 3, 6, and 8 days following the surgery, the dressings and device were removed and the wound site was photographed. Planimetric analysis of photographic data are performed. All the animals were redressed by replacing all the Delnet™ (apertured film) material with new pieces. The DelNet pieces were preserved from Day 3 in formalin. On day 10, the dressings were removed and the wound site was inspected and photographed. If significant healing has occurred in at least some animals, all animals would be euthanized and all wound areas would be harvested, and preserved in formalin. The average wound areas for each condition over time were compared. Histologic analysis of explanted devices and tissues were performed. The wound bed cross sections were stained using hematoxylin and eosin stains. The wound bed cross sections for human involucrin were stained.

The healing process for Group 2 (Hyperglycemic with Keratinocytes) was observed to be qualitatively different from that observed in Groups 1 and 3 (untreated). At the first dressing change, day 3 post-wound, it was noted that the treated group appeared to have a thin layer of epidermis forming over the wound bed compared to the untreated group. The wound area of the untreated hyperglycemic rat at day 3 post-wound demonstrated that the wound is still bloody and open (FIG. 17(B)(I)). The photo of the hyperglycemic rat treated with keratinocytes at day 3 post-wound demonstrated a wound that appeared dry and covered (FIG. 17(B)(II)).

Figure 17A:
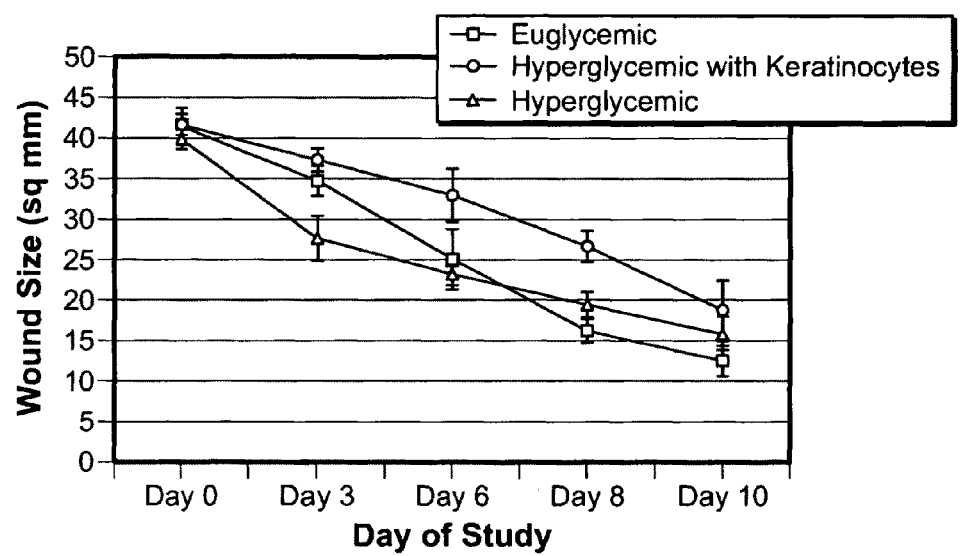
FIG. 17 shows wound area measurements in hyperglycemic rats treated with keratinocytes compared to the controls (A) and the qualitative differences in wound healing in hyperglycemic mice treated with keratinocytes (II) on apertured films versus untreated (I) hyperglycemic mice (B).
Figure 17B:
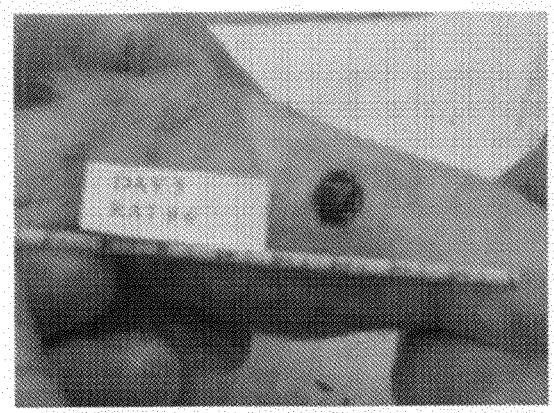
Figure 17B:

There is a significant difference in the area within the wound margin for Group 2 compared to Groups 1 and 3 after day 3 post-wound (FIG. 17). The wounds in the treated group (Group 2) appear to have undergone less contraction than the other two groups. Histological analysis demonstrated that all groups displayed wounds with full epidermal coverage and some form of granulation tissue with re-emerging dermal tissue. The wound area measurements were therefore based on the original wound margin. The original wound margins in the treated group have contracted significantly less than the two non-treated groups. Keratinocytes cultured to Delnet™ (apertured film) likely prevents wound contraction and therefore, is capable of reducing scaring during the wound healing process for large wounds.

Example 9

Comparison of Human Vascular Smooth Muscle Cell Cultures Initiated on Cytoline-1 Microcarriers vs. Vascular Smooth Muscle Cell Cultures Initiated on DelNet™ Material This example compares human vascular smooth muscle cell growth on two different substrates—Cytoline-1 Microcarrier Beads and Delnet™ (apertured film) material. The metabolic activity of smooth muscle cells grown on the two substrates are measured over time post-seed.

The experiment was initiated by thawing one vial of cryopreserved human aortic vascular smooth muscle cell (ATCC Cat # CRL-1999, lot 3731638), $0.5 \times 10^6$ cells/vial, and was seeded to one T-75 flasks at passage 16. The flask fed with 25 mL of Medium 231 (Cascade Biologics, Portland Oreg.) supplemented with SMGS (Cascade Biologics, Portland Oreg.). The flask was gassed with 10% $CO_2$ and incubated at 37° C. with sealed cap. The flask was fed with 25 mL of Medium 231 supplemented with SMGS growth media every 2-3 days throughout passage 16. The cells were microscopically observed at each feed and the percentage of flask surface confluence was estimated.

After the cells reached approximately 80% confluence, the cells were harvested by trypsinization and it was followed by trypsin neutralization to yield a uniform cell suspension in Medium 231 supplemented with SMGS growth media. The cells in suspension were counted using a hemacytometer to determine the total harvest yield. The cells were passaged at passage 17 at $1 \times 10^6$ cells/T-162 flask. The passage 17 was cultured and harvested as described herein.

The cell suspensions in Medium 231 supplemented with SMGS from the passage 17 harvest were prepared as follows:

| Cell Suspension | Concentration (cells/mL) | Minimum Final Volume (mL) |
|---|---|---|
| A | $1.00 \times 10^6$ | 30 |
| B | $0.50 \times 10^6$ | 32 |
| C | $0.75 \times 10^6$ | 32 |

About thirty 1.5"×1.5" pieces of double layered Delnet™ (apertured film) were placed in each of ten 100 mm Petri dishes. About 30 mL of Cytoline-1 Microcarriers, prepared according to manufacturer's instructions was placed in one T-175 flask. About 30 mL of Cell Suspension "A" was transferred to the 30 mL of microcarrier beads. About 2 mL of Cell Suspension "B" was transferred to each of the 15 pieces of double layered Delnet. It was attempted to keep the entire 2 mL on the Delnet™ (apertured film). About 2 mL of the Cell Suspension "C" was transferred to each of the 15 pieces of double layered Delnet™ (apertured film). All the samples were allowed to incubate at room temperature for 1 hour.

Each piece of double layered Delnet™ (apertured film) was transferred to 150 mL bottles containing 175 mL (filled) of Medium 231 supplemented with SMGS growth media. The caps were sealed and incubated at 37° C.

About 2 mL each of the Cytoline-1 Microcarriers was transferred to each of fifteen 150 mL bottles containing 175 mL (filled) of Medium 231 supplemented with SMGS growth media. The caps were sealed and incubated at 37° C.

The following samples were prepared (15 samples per condition):

|  | A | B | C |
|---|---|---|---|
| Microcarriers | $2.0 \times 10^6$ | N/A | N/A |
| Delnet | N/A | $1.0 \times 10^6$ | N/A |
| Delnet | N/A | N/A | $1.5 \times 10^6$ |

At days 1, 7, 14, 28 post-seed, the metabolic activity was determined in three samples from each condition. The seeding density were not uniform that would have given a similar day 1 metabolic activity. The day 1 metabolic activity for the seeding density of cells on beads was higher than those chosen for cells on Delnet™ (apertured film).

Figure 16:
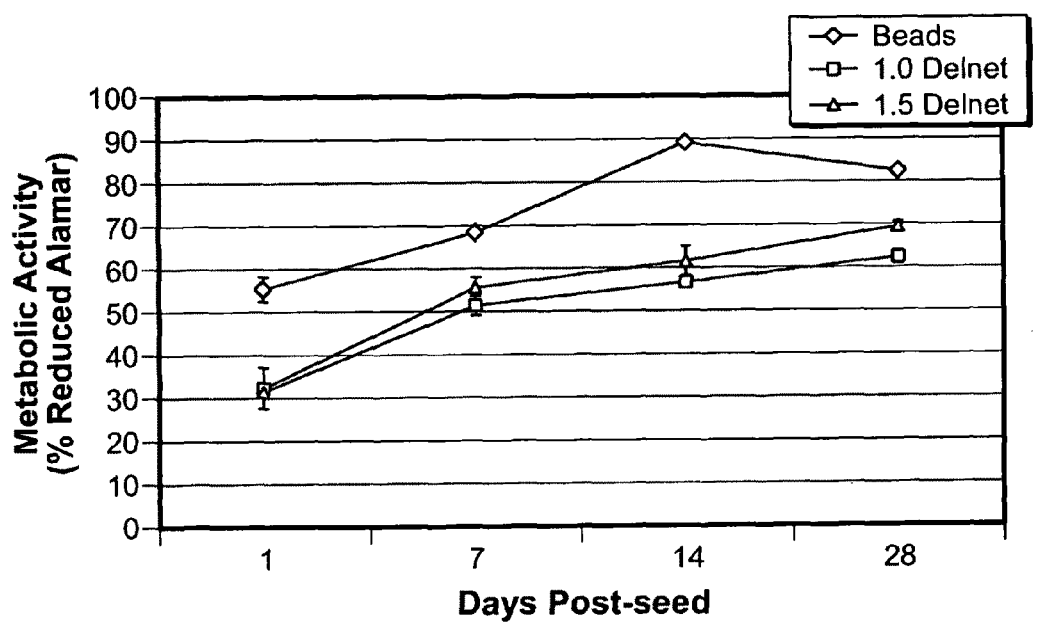
FIG. 16 shows a comparison of human vascular smooth muscle cell cultures initiated on Cytoline-1 microcarriers (beads) vs. vascular smooth muscle cell cultures initiated on a flexible support material such as a Delnet™ (apertured film) material at two seeding concentrations.

The data on FIG. 16 demonstrates that the smooth muscle cells grow well on the beads and are comparable to smooth muscle cells cultured on the Delnet™ (apertured film). The Delnet™ (apertured film) material was seeded with two different cell suspensions of lower concentration than those used for seeding the Cytoline-1 Microcarriers to have a comparison that similar metabolic activity at day 1. The differences at day 1 could be caused by variable attachment to each substrate and by the fact that the beads and the Delnet™ (apertured film) have different sized large pores through which cells can pass and not come in contact with the substrate.

Example 10

Cultivation of Human Epithelial Keratinocytes on Delnet™ (Apertured Film) Treated with a Bioactive Polymer This example demonstrates that human epithelial keratinocytes (HEK) was successfully cultivated on Delnet™ (apertured film) treated with a bioactive polymer, a recombinant collagen matrix. As demonstrated herein, HEK was cultivated successfully on untreated Delnet™ (apertured film). This experiment demonstrates cultivation of HEK on Delnet™ film) coated with a recombinant collagen matrix product prior to seeding.

One square piece of two-ply, sterile Delnet™ (apertured film) (~16 $cm^2$) was placed in each of twenty 10 cm petri dishes. The coating matrix (P/N R-011-K, Cascade Biologics, Portland, Oreg.) was prepared by adding each 500 uL matrix aliquot to its respective 50 mL diluent solution bottle and by mixing thoroughly. About 10 mL of the matrix mixture was added immediately to each of ten Delnet™ (apertured film) pieces. About 10 mL DPBS (P/N D8537, Sigma, St. Louis, Mo.) was added to the remaining ten DelNet pieces. All Delnet™ (apertured film) pieces were incubated at room temperature for 30 minutes. All 20 Delnet™ (apertured film) pieces were transferred to new petri dishes, preserving the orientation of the material.

About 40 mL suspension of P3 HEK at $0.25\times10^6$ cells per mL of KGM-2 (P/N CC-3107, Lonza, Portsmouth, N.H.) was prepared. About 2 mL of this suspension was seeded onto each Delnet™ (apertured film) piece and was incubated at room temperature for 45 minutes.

Figure 15B:
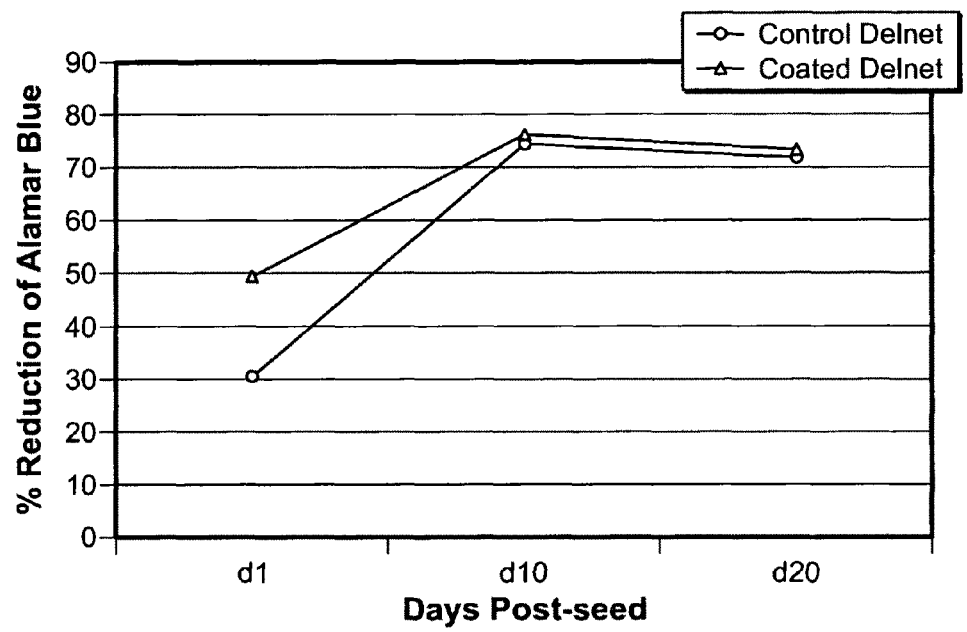

About 175 mL KGM-2 was added to each of 20 polystyrene bottles (P/N 431175, Corning, Lowell, Mass.). All Delnet™ (apertured film) pieces were transferred to bottles and by orienting the pieces to float cell-side down. The bottles were sealed and stored at 37° C. Metabolic activity was determined in three samples from each condition at the following time-points: Day 1, Day 10, Day 20. The percentage of Alamar Blue reduction at each time point for each sample was calculated. FIG. 15B demonstrates that human epithelial keratinocytes grow on Delnet™ (apertured film) treated with a bioactive polymer, e.g., collagen matrix. Other suitable polymers include for example, fibronectin or any component of the extracellular matrix (ECM).

Example 11

Culture of Human Keratinocytes on Apertured Film—Metabolic Activity and Device Ex-Plantation Assay Human keratinocytes were cultured to end of passage 4 in tissue culture flasks. The cultured keratinocytes were harvested at the end of passage 4 and were seed to 1.5"×1.5" double layer Delnet pieces at $2\times10^5$ cells per piece. Each piece of cultured Delnet in was packaged in 175 mL of EpiLife Animal Product-free feed media. Each container was sealed and incubated at 37° C. At the following time points post-seed to Delnet (day 1, 7, 14, 21, 28) two of the cultured Delnet pieces were removed and metabolic activity was measured using Alamar Blue reduction assay. Following metabolic activity measurements, each piece was aseptically transferred to a 100 mm tissue culture dish with cells facing the culture surface. Gently 20 mL of EpiLife Animal Product-free feed media was added to each dish. Incubation at 37° C., 5% $CO_2$ for 4 days was performed. The Delnet piece was removed from each dish and the media in each dish was replaced with 20 mL of fresh EpiLife Animal Product-free feed media every 2-3 days. After 7 days from removing the Delnet piece from the dish, the dish was fixed in 100% isopropanol and then stain with 0.01 g/mL Acid Fuchsin in PBS. The stained cells on the dishes were photographed at each time point.

This study demonstrated that human keratinocytes migrate off of the apertured film material, attach to a secondary support surface (e.g., the dish) and proliferate on the secondary surface to produce keratinocyte colonies, e.g., day 7 and day 14 pictures (FIG. 7). Around day 21 and 28, the keratinocytes stop forming colonies on the secondary surface. This result indicates that cultured keratinocytes are capable of migrating out of a suitable flexible support material such as an apertured film (e.g., Delnet™) and reach a targeted delivery site, for example, wound surface. Thus, the apertured support material seeded with keratinocytes provide a wound healing device wherein the keratinocytes is readily delivered to a treatment site.

Example 12

Culturing Stems Cells on Apertured Film Material

Figure 14:
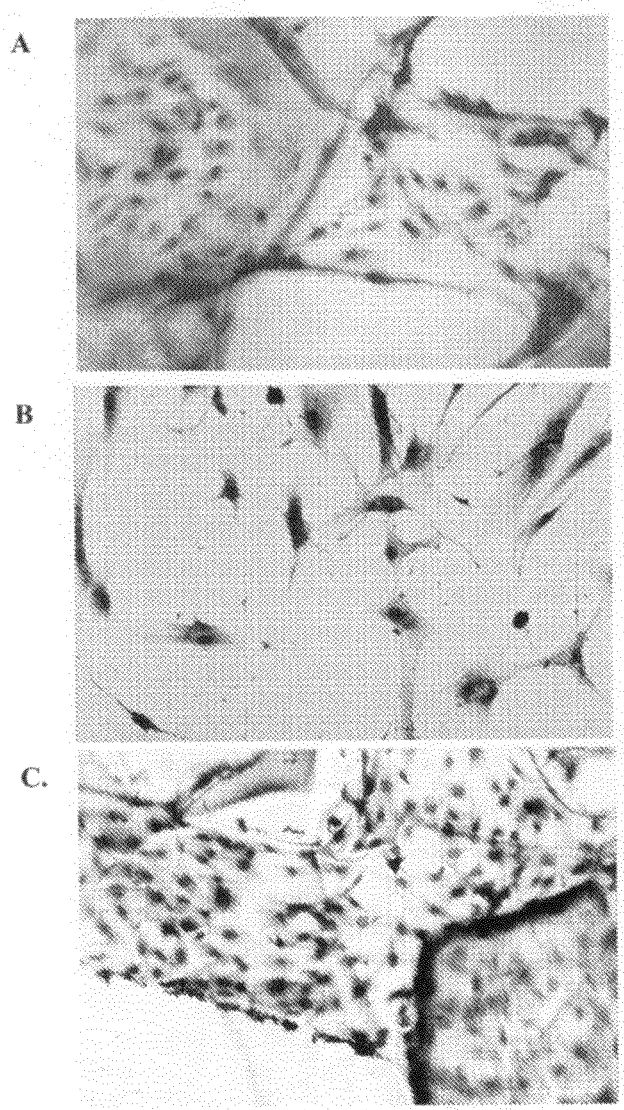
FIG. 14 shows the growth of mesenchymal stem cells on a collagen coated double layered mesh or an apertured film (Delnet™)) (A). Human Mesenchymal stem cells (Cambrex PT-2501) growing in a 6-well tissue culture flask and stained with Giemsa stain are shown in a photograph at 200× magnification (B) and mouse mesenchymal stem cells (C).

Human mesenchymal stem cells (Cambrex PT-2501) were grown in complete hMSc media (Cambrex PT-3238 basal media supplemented with PT-4105) to passage two. 200 µl of a suspension of approximately $1\times10^5$ cells/ml was placed on a collagen coated double layered mesh. The cells were allowed to attach to the mesh for 40 min in a 37° C. incubator. The mesh was then placed cell side down into a bottle of 100 ml complete media. The mesh was removed the next day and cells were stained with Giemsa stain. The cells were photographed is at 200× magnification (FIG. 14A). Human mesenchymal stem cells (Cambrex PT-2501) growing in a 6-well tissue culture flask were stained with Giemsa stain and photographed at 200× magnification (FIG. 14B).

Mouse mesenchymal stem cells (ATCC #CCL-226) were grown in Eagle's Basal media supplemented with 1.5 g/L sodium bicarbonate and 10% heat inactivated FBS. Cells (500 µL of $1\times10^5$ cells/ml) were placed onto a double layered non-coated mesh in 100 mm petri dish. Cells were allowed to attach for 30 min. in hood and then 5 ml media was added. The plate was placed in a 37 C incubator. 5% $CO_2$ for 6 days, media was change every 3 days. The mesh was then removed and stained with Giemsa. Mesh was photographed at 200× (FIG. 14C).

This example demonstrates the feasibility of culturing stem cells on a flexible support material such as for example, an apertured film material like a Delnet™ bag.

MATERIALS AND METHODS

Alamar Blue Assay
Reagent Preparation:
1.1.1 Prepare 5% Alamar Blue Solution:
    1.1.1.1 Aseptically place 125 mL PETG bottle, 250 mL filter unit, 50 mL pipet, 5 mL pipet, Alamar blue, and KC111 in BSC.
        2.1.1.1.1 Record control/lot numbers and expiration dates for the Alamar Blue and the KC111 on Step 8.1.
    1.1.1.2 To a 125 mL bottle add 95 mL of KC111 and 5 mL Alamar Blue.
    1.1.1.3 Swirl gently to mix.
    1.1.1.4 Add Alamar Blue solution to the top of a bottle top filter unit.
    1.1.1.5 Attach vacuum source and filter the solution.
    1.1.1.6 Tightly cap the bottle and cover the bottle with aluminum foil.
    1.1.1.7 Store at room temperature.
    1.1.1.8 Use on date of preparation. Discard unused portion.
2.2 Sample Preparation:
NOTE: Staining procedure to take place inside a BSC.
  2.2.1 Obtain test sample and negative control bottle.
  2.2.2 Obtain prepared KC111.
  2.2.3 Record product lot number and assembly date on the Test Record.
  2.2.4 Obtain 5% Alamar Blue Solution prepared as described above.
  2.2.5 Aseptically place sample and negative control into BSC.
  2.2.6 Label five 125 mL PETG bottles "Media Only", "Media+Microcarriers", "Alamar Blue Only", Alamar Blue+Microcarriers", and "Test" being sure to include product lot number on the bottles.
  2.2.7 "Media only" Sample:
    1.2.7.1 Add 30 mL KC111 to the "Media Only" bottle.
  2.2.8 "Media+substrate" Sample:
    1.2.8.1 Using a 10 mL wide mouth pipet, remove 2 mL of Cytoline-1 beads from negative control bottle and place into the "Media+Substrate" bottle.

1.2.8.2 Pipet off the media and replace with 30 mL KC111.
1.2.8.3 Swirl the bottle gently to submerge all the substrates.
2.2.9 "Alamar Blue Only" Sample:
1.2.9.1 Add 30 mL of Alamar blue to the "Alamar Blue Only" bottle.
2.2.10 "Alamar Blue+substrates" Sample: Alamar blue and the substrate, e.g., DelNet bag.
2.2.11 "Test" Sample:
2.2.12 5% Alamar Blue Addition:
1.2.12.1 Pipet off the media from the test sample in the Alamar Blue+substrate" and "Test" bottles using separate pipettes.
1.2.12.2 Add 30 mL of the 5% Alamar Blue Solution prepared above to each bottle.
1.2.12.3 Swirl the bottle gently to submerge all the microcarriers.
1.2.12.4 Loosen the bottle caps before transferring to the incubator.
2.2.13 Transfer the samples to 10% $CO_2$ 37° C. incubator. Protect from light. Incubate for 24 hours (±15 minutes).
2.3 Metabolic Activity Determination:
2.3.1 Sample preparation after 24 hour (±15 minutes) incubation at 36.5° C.±2° C. 10% $CO_2$:
1.3.1.1 Turn on plate reader.
1.3.1.2 Obtain a 96 well plate.
1.3.1.3 Swirl the bottle gently to ensure uniform samples.
1.3.1.4 Pipette 200 μL from each sample (media, media+substrates, Alamar blue only, Alamar blue+substrates, and test) into a well of a 96 well plate. Samples are run in triplicate.
1.3.1.5 Document sample placement to be analyzed on Step 8.1.
2.3.2 Open Skanit Software.
2.3.3 Initiate a new session.
1.3.3.1 Go to "Session" menu and select "New"
1.3.3.2 In the popup window, select "User Defined Protocol."
1.3.3.3 Highlight "Alamar Blue Template"
1.3.3.4 Type in Session and Protocol Name using the following format: ABYYYY-MM-DD.
1.3.3.5 Click "Next"
1.3.3.6 In the "Plate Layout Options" field, select "Attach to Existing"
1.3.3.7 From the list, select "Alamar Blue Template"
1.3.3.8 Click "Next"
1.3.3.9 Click "Finish"
2.3.4 Execute Session.
2.3.4.1.1 Go to "Execute" menu and select "Run plate out."
2.3.4.1.2 Place plate on shelf of plate reader.
2.3.4.1.3 Go to "Execute" menu and select "run plate in."
2.3.4.1.4 Save session using the following format: ABYYYY-MM-DD.
2.3.4.1.5 Go to "Execute" menu and select "Session."
2.3.4.1.6 Select "Start."
2.3.4.1.7 Save changes using the following format: ABYYYY-MM-DD.
1.3.4.2 Results Report:
2.3.4.2.1 Select "Report" tab.
2.3.4.2.2 Print report.
2.3.4.2.3 Save data 2.3.5 Interpretation of Results:
1.3.5.1 Open the Alamar blue analysis template.
1.3.5.2 Enter plate data into the template.
2.3.5.2.1 Obtain the average of the background wells for the "Media Only" and the Media+substrates" for each wavelength.
2.3.5.2.2 Subtract background from the corresponding wavelength for the "Alamar Blue Only" and the "Alamar Blue+substrate" readings.
2.3.5.2.2.1 Obtain the average for the negative control wells minus the background.
2.3.5.2.3 Subtract background from the corresponding wavelength for the test samples.
2.3.5.2.3.1 Obtain the average for the test samples minus the background.
2.3.5.2.4 Insert averages into the following formula to calculate the % reduced for the negative control. This is used as the assay control.
% Reduced=100×((117216×Average "Alamar Blue+substrates" @ 570λ)−(80586×Average "Alamar Blue+substrates" @ 600λ))/((155677× Average "Alamar Blue Only" @ 600λ)−(14652× Average "Alamar Blue Only" @ 570λ))
2.3.5.2.5 Insert averages into the following formula to calculate the % reduced for the test sample. % Reduced=100×((117216×Average "Test Sample" @ 570λ)−(80586×Average "Test Sample" @ 600λ))/((155677×Average "Alamar Blue+Substrates" @ 600λ)−(14652×Average "Alamar Blue+ Substrates" @ 570λ))
1.3.5.3 The assay is acceptable if the negative control % reduction is <10%.

PUBLICATIONS CITED

These publications are incorporated by reference to the extent they relate to materials or methods disclosed herein.

Kuznetsov (2006) An electrochemical method for measuring metabolic activity and counting cells, *Applied Biochemistry and Microbiology*, 42 (5): 525-533.

Mansbridge J et al. (1998) Three-dimensional fibroblast culture implant for the treatment of diabetic foot ulcers: metabolic activity and therapeutic range. *Tissue Engineering;* 4:403-14.

The invention claimed is:
1. A wound healing device comprising:
(i) a flexible support material that provides a biocompatible surface for cellular growth comprising an inner layer of ethylene vinyl acetate (EVA) and an outer layer of high density polyethylene (HDPE), the flexible support material having pores with diameters ranging from 0.1 μm to 0.4 μm, said flexible support material being capable of being directly applied on to a wound surface; and
(ii) a population of cells selected from the group consisting of keratinocytes, fibroblasts, endothelial cells, muscle cells, melanocytes, macrophages, stem cells or a combination thereof cultured directly on the inner layer of the flexible support material.
2. The wound healing device of claim 1, wherein the flexible support material is associated with a growth promoting compound.
3. The wound healing device of claim 1, wherein the population of cells are provided in the form of a cell culture medium and the cell culture medium comprises a first medium component selected from the group consisting of:

an animal product-free media system;
Medium 106 supplemented with LSGS;
EpiLife medium; and
EpiLife animal product-free medium.

4. The wound healing device of claim 1, wherein the flexible support material forms a bag-like structure.

5. The wound healing device of claim 1, wherein the cells are seeded on to the flexible support material at a density of about $10^2$ cells to about $10^7$ cells per 16 cm$^2$ support material.

6. The wound healing device of claim 1, comprising cultures of different cell populations on the flexible support material to form a tissue engineered from the cells.

7. The wound healing device of claim 1, wherein the flexible support with the cells is applied to an injured tissue site to repair the tissue.

* * * * *